(12) United States Patent
Pratt et al.

(10) Patent No.: US 9,696,305 B2
(45) Date of Patent: Jul. 4, 2017

(54) ANTIBODY RESPONSE PHENOTYPING

(71) Applicant: Puget Sound Blood Center, Seattle, WA (US)

(72) Inventors: Kathleen Pratt, Bethesda, MD (US); Kenneth B. Lewis, Seattle, WA (US)

(73) Assignee: Bloodworks, Seattle, WA (US)

( * ) Notice: Subject to any disclaimer, the term of this patent is extended or adjusted under 35 U.S.C. 154(b) by 38 days.

(21) Appl. No.: 14/354,476

(22) PCT Filed: Oct. 31, 2012

(86) PCT No.: PCT/US2012/062766
§ 371 (c)(1),
(2) Date: Apr. 25, 2014

(87) PCT Pub. No.: WO2013/066986
PCT Pub. Date: May 10, 2013

(65) Prior Publication Data
US 2014/0296105 A1    Oct. 2, 2014

Related U.S. Application Data

(60) Provisional application No. 61/553,660, filed on Oct. 31, 2011.

(51) Int. Cl.
| | |
|---|---|
| G01N 31/00 | (2006.01) |
| G01N 33/53 | (2006.01) |
| G01N 33/564 | (2006.01) |
| G01N 33/543 | (2006.01) |
| G01N 33/86 | (2006.01) |

(52) U.S. Cl.
CPC ..... *G01N 33/564* (2013.01); *G01N 33/54373* (2013.01); *G01N 33/86* (2013.01)

(58) Field of Classification Search
CPC .......... A61K 39/3955; A61K 2039/505; A61K 2300/00; C07K 16/30; C07K 2317/74; G01N 2333/726; G01N 2500/02
See application file for complete search history.

(56) References Cited

U.S. PATENT DOCUMENTS

| | | |
|---|---|---|
| 2003/0040027 A1 | 2/2003 | Ritter et al. |
| 2007/0049733 A1 | 3/2007 | Zurlo et al. |
| 2008/0227691 A1* | 9/2008 | Ostergaard ........... C07K 14/755 514/1.1 |
| 2011/0183363 A1 | 7/2011 | Fischer et al. |
| 2011/0223645 A1 | 9/2011 | Hansen et al. |
| 2013/0288387 A1 | 10/2013 | Blancher et al. |

FOREIGN PATENT DOCUMENTS

WO    WO 2006/103298 A2 * 10/2006 ........... C07K 14/755

OTHER PUBLICATIONS van Heiden et al. Blood, vol. 118, No. 13, Sep. 29, 2011, pp. 3698-3707.*
Wootla et al. The Journal of Immunology, 2008, vol. 180, pp. 7714-7720.*
Saenko et al. (Vox Sanguinis, 2002, vol. 83, pp. 89-96).*
Saenko et al. (Journal of Chromatography A, vol. 852, 1999, pp. 59-71).*
Jacquemin et al. (Blood, vol. 92, No. 2, Jul. 15, 1998, pp. 496-506).*
Buchacher et al., "Purification of Intravenous Immunoglobulin G from Human Plasma—Aspects of Yield and Virus Safety," Biotechnology Journal, Feb. 1, 2006, pp. 148-163, vol. 1.
PCT International Search Report and Written Opinion, PCT Application No. PCT/US2012/062766, Mar. 7, 2013, 19 pages.
PCT Invitation to Pay Additional Fees, PCT Application No. PCT/US2012/062766, Jan. 4, 2013, 2 pages.

* cited by examiner

*Primary Examiner* — Lisa Cook
(74) *Attorney, Agent, or Firm* — Fenwick & West LLP

(57) ABSTRACT

Disclosed herein are methods, systems, mediums, and kits for use in phenotyping antibody responses via devices such as surface plasmon resonance devices. Such phenotypes can include total target-specific antibody titers, quantitative isotype distribution of the target-specific antibodies, and/or epitope specificity of the target-specific antibodies. Other methods, systems, mediums, and kits are also disclosed.

11 Claims, 4 Drawing Sheets

ANTIBODY RESPONSE PHENOTYPING

CROSS REFERENCE TO RELATED APPLICATIONS

This application is a 371 of International Application No. PCT/US12/62766 filed Oct. 31, 2012 which claims the benefit of U.S. Provisional Application No. 61/553,660, filed Oct. 31, 2011, both of which are incorporated by reference herein in their entirety.

STATEMENT REGARDING FEDERALLY SPONSORED RESEARCH OR DEVELOPMENT

This invention was made with government support under NIH 1RC2 HL101851 awarded by National Heart, Lung and Blood Institute as part of the American Recovery and Reinvestment Act (ARRA). The government has certain rights in the invention.

BACKGROUND

Surface Plasmon Resonance (SPR) offers a detection platform that is versatile, robust, and amenable to complex, multiplexed measurements of samples. The relative speed with which SPR sensorgrams can be generated and analyzed also makes this technique suitable for medium- to high-throughput analysis of multiple samples. Described herein is the use of an SPR assay to define phenotypes of allo- and autoimmune antibody responses based on antigen-specific immunoglobulin subclass distribution and epitope specificity.

SUMMARY

Disclosed herein is a method for determining the phenotype of a target antigen-specific antibody response in a subject, comprising: contacting a biorecognition surface with a sample from the subject comprising a plurality of target antigen-specific antibodies to produce a contacted surface; contacting the contacted surface with a probe antibody specific for the target antigen-specific antibodies under saturation conditions; and determining, by a biosensor device, the phenotype of the target antigen-specific antibody response in the subject.

In some aspects, the phenotype is total target antigen-specific antibody titers; quantitative isotype distribution of the target antigen-specific antibodies; and/or epitope specificity of the target antigen-specific antibodies. In some aspects, the isotype of the quantitative isotype distribution of the target antigen-specific antibodies is selected from the group consisting of IgG, IgG1, IgG2, IgG3, IgG4, IgA, IgM, and IgE. In some aspects, the biosensor device is a surface plasmon resonance (SPR) device.

In some aspects, the sample is a plasma sample. In some aspects, the sample is a plasma sample treated with caprylic acid (CA).

In some aspects, the biorecognition surface comprises a surface coupled with a capture agent specific for the target antigen, and wherein the target antigen is contacted by the capture agent. In some aspects, the capture agent is a capture antibody. In some aspects, the method further comprises coupling a capture agent specific for the target antigen to a surface and contacting the capture agent with the target antigen to produce the biorecognition surface.

In some aspects, the subject is a mammal. In some aspects, the subject is a human. In some aspects, the subject is a subject having hemophilia A. In some aspects, the target antigen-specific antibodies from the sample are anti-Factor VIII (FVIII) antibodies. In some aspects, the target antigen is FVIII.

Also described herein is a method of producing a prepared surface for use in a biosensor device, comprising: obtaining a biorecognition surface contacted with a plurality of target antigen-specific antibodies from a sample from a subject; and contacting the biorecognition surface with a probe antibody specific for the target antigen-specific antibodies under saturation conditions to produce the prepared surface.

In some aspects, the biosensor device is a surface plasmon resonance (SPR) device. In some aspects, the sample is a plasma sample. In some aspects, the sample is a plasma sample treated with caprylic acid (CA). In some aspects, the biorecognition surface comprises a surface coupled with a capture agent specific for the target antigen, and wherein the target antigen is contacted by the capture agent.

In some aspects, the subject is a mammal. In some aspects, the subject is a human. In some aspects, the subject is a subject having hemophilia A. In some aspects, the target antigen-specific antibodies are anti-Factor VIII (FVIII) antibodies. In some aspects, the target antigen is FVIII.

Also described herein is a surface produced by a method described herein.

Also described herein is a computer-implemented method for scoring a sample obtained from a subject, wherein the score indicates the phenotype of a target antigen-specific antibody response in the subject, comprising: obtaining, by a biosensor device, a dataset associated with the sample, wherein the sample is obtained from the subject, wherein the dataset comprises target antigen capture level data, capture agent binding level data, and secondary antibody binding level data; and determining, by a computer processor, a score from said dataset using an interpretation function, wherein said score is indicative of the phenotype of the target antigen-specific antibody response in the subject.

In some aspects, the method further comprises, determining, by a computer processor, the phenotype of the target antigen-specific antibody response in the subject, based on said score.

In some aspects, the phenotype is total target antigen-specific antibody titers; quantitative isotype distribution of the target antigen-specific antibodies; and/or epitope specificity of the target antigen-specific antibodies. In some aspects, the biosensor device is a surface plasmon resonance (SPR) device.

In some aspects, the sample is a plasma sample. In some aspects, the sample is a plasma sample treated with caprylic acid (CA). In some aspects, the subject is a mammal. In some aspects, the subject is a human. In some aspects, the subject is a subject having hemophilia A. In some aspects, the target antigen-specific antibodies are anti-Factor VIII (FVIII) antibodies.

In some aspects, obtaining said dataset associated with said sample comprises obtaining said sample and processing said sample to experimentally determine said dataset. In some aspects, obtaining said dataset associated with said sample comprises receiving said dataset directly or indirectly from a third party that has processed said sample to experimentally determine said dataset.

Also described herein is a method of preparing a sample for use in a biosensor device, comprising: obtaining the sample, wherein the sample comprises plasma from a subject; and contacting the sample with an amount of caprylic acid (CA) sufficient to precipitate non-IgG proteins and von Willebrand factor.

In some aspects, the sample further comprises sodium acetate. In some aspects, the method further comprises removing the precipitate. In some aspects, the method further comprises neutralizing the sample. In some aspects, neutralizing the sample comprises contacting the sample with HEPES, sodium chloride, and carboxy methyl dextran (CMD).

Also described herein is a CA treated sample prepared by a method described herein.

Also described herein is a system, said system comprising: a biorecognition surface comprising a surface contacted with a capture agent, the capture agent contacted with a target antigen, the target antigen contacted with a plurality of target antigen-specific antibodies from a sample from a subject, and the target-specific antibodies contacted with a probe antibody under saturation conditions; and a biosensor device for determining the phenotype of the target antigen-specific antibodies.

In some aspects, the phenotype is total target antigen-specific antibody titers; quantitative isotype distribution of the target antigen-specific antibodies; and/or epitope specificity of the target antigen-specific antibodies. In some aspects, the isotype of the quantitative isotype distribution of the target antigen-specific antibodies is selected from the group consisting of IgG, IgG1, IgG2, IgG3, IgG4, IgA, IgM, and IgE. In some aspects, the biosensor device is a surface plasmon resonance (SPR) device.

In some aspects, the sample is a plasma sample. In some aspects, the sample is a plasma sample treated with caprylic acid (CA). In some aspects, the capture agent is a capture antibody.

In some aspects, the subject is a mammal. In some aspects, the subject is a human. In some aspects, the subject is a subject having hemophilia A. In some aspects, the target antigen-specific antibodies from the sample are anti-Factor VIII (FVIII) antibodies. In some aspects, the target antigen is FVIII.

Also described herein is a system comprising a processor for carrying out one or more methods described herein.

Also described herein is a computer-readable storage medium storing computer-executable program code, said program code comprising: program code for storing a dataset associated with a sample obtained from a subject, wherein the dataset comprises target antigen capture level data, capture agent binding level data, and secondary antibody binding level data; and program code for analyzing said dataset to determine a score from said dataset using an interpretation function, wherein said score is indicative of the phenotype of a target antigen-specific antibody response in the subject.

Also described herein is a computer-readable storage medium storing computer-executable program code for carrying out one or more methods described herein.

Also described herein is a kit, comprising: a set of reagents comprising a biorecognition surface for determining from a sample obtained from a subject the phenotype of a target antigen-specific antibody response in the subject; and instructions for determining from the sample obtained from the subject the phenotype of the target antigen-specific antibody response in the subject using a biosensor device.

In some aspects, the phenotype is total target antigen-specific antibody titers; quantitative isotype distribution of the target antigen-specific antibodies; and/or epitope specificity of the target antigen-specific antibodies. In some aspects, the isotype of the quantitative isotype distribution of the target antigen-specific antibodies is selected from the group consisting of IgG, IgG1, IgG2, IgG3, IgG4, IgA, IgM, and IgE. In some aspects, the biosensor device is a surface plasmon resonance (SPR) device. In some aspects, the sample is a plasma sample. In some aspects, the sample is a plasma sample treated with caprylic acid (CA). In some aspects, the biorecognition surface comprises a surface coupled with a capture agent specific for the target antigen, and wherein the target antigen is contacted by the capture agent. In some aspects, the capture agent is a capture antibody. In some aspects, the kit further comprises instructions for coupling a capture agent specific for the target antigen to a surface and contacting the capture agent with the target antigen to produce the biorecognition surface.

In some aspects, the subject is a mammal. In some aspects, the subject is a human. In some aspects, the subject is a subject having hemophilia A. In some aspects, the target antigen-specific antibodies from the sample are anti-Factor VIII (FVIII) antibodies. In some aspects, the target antigen is FVIII.

Also described herein is a kit including one or more reagents and/or instructions for carrying out one or more of the methods described herein.

BRIEF DESCRIPTION OF THE SEVERAL VIEWS OF THE DRAWINGS

These and other features, aspects, and advantages of the present invention will become better understood with regard to the following description, and accompanying drawings, where.

DETAILED DESCRIPTION OF THE INVENTION

Compositions

Figure 1:
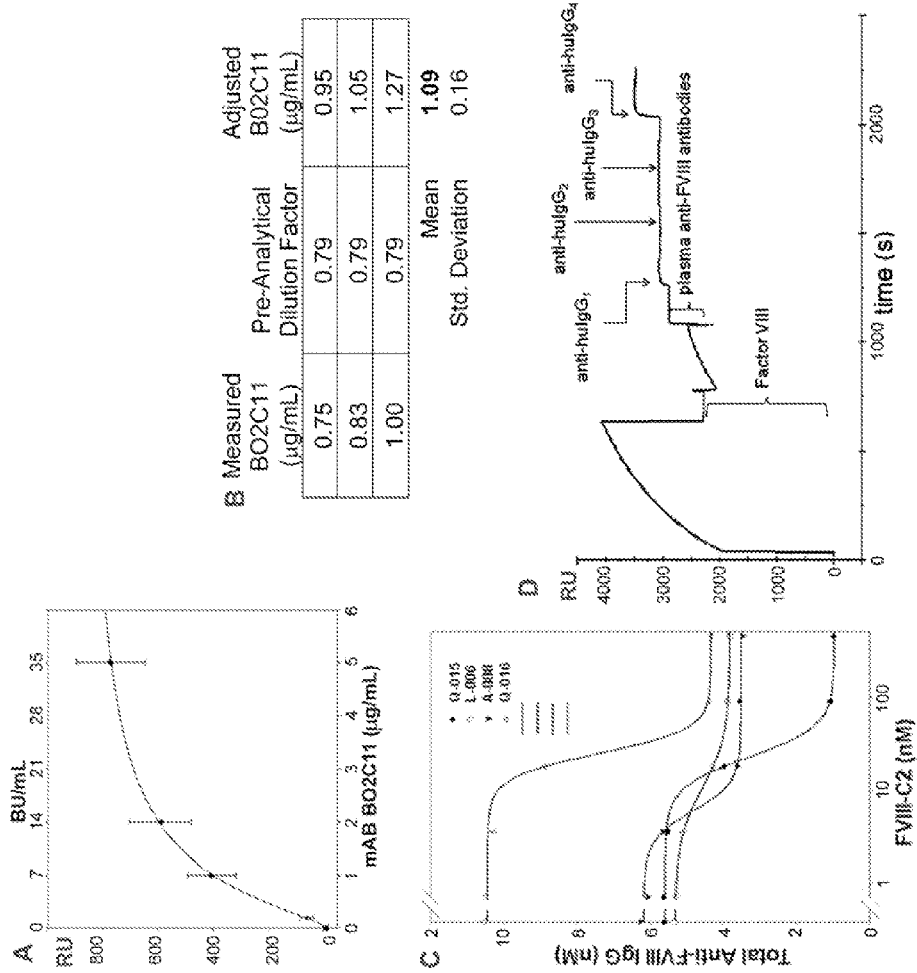
FIG. 1: A) Combined BO2C11 calibration curves obtained from independent SPR runs. FVIII inhibitor titers in Bethesda units (BU)/ml from specific activity of BO2C11=7,000 BU/mg [11]. B) Spike recovery of independent samples of 1 µg/ml B02C11 added to inhibitor negative plasma and treated with CA; the measured RU values were converted to concentration in µg/ml based on calibration curves generated for BO2C11 using inhibitor-negative plasma. The 'inhibitor negative' plasma used in these experiments showed no evidence of neutralizing or non-neutralizing anti-FVIII antibodies when tested using the SPR capture format (not shown). C) Titration Inhibition curves showing addition of increasing concentrations of recombinant FVIII-C2 to CA-treated plasma from 4 inhibitor-positive subjects. The sample from subject Q-016 was diluted first in order to bring the total anti-FVIII antibody titer below 10 nM. The FVIII-C2-specific antibody fraction was saturated above 100 nM FVIII-C2 in all 4 samples. D) Representative binding curve (sensorgram) depicting the 600 sec. injection and capture of FVIII (2277 RU), 300 sec. injection of test plasma and capture of human anti-FVIII antibodies (839 RU), and sequential 120 sec. injections and binding of mouse anti-human $IgG_1$ (191 RU), $IgG_2$ (75 RU), $IgG_3$ (−9 RU), and $IgG_4$ (558 RU). Note that uncompensated refractive index mismatches caused offsets in the binding curve during the FVIII and test plasma injections. The annotated report points were used to obtain the quantitative results summarized in Tables 1 & 2.

In some aspects, a surface can be used to phenotype a target-antigen specific immune response in a subject of interest. As used herein, the term "surface" means a material in the solid-phase that interacts with reagents in the liquid phase by heterogeneous reactions. Surfaces can be derivatized with ligands by covalent or non-covalent bonding through one or more attachment sites, thereby "immobilizing" the ligand to the surface. The term includes, but is not limited to, solid supports, glass surfaces, metal-coated glass surfaces, such as gold-coated, and modifications thereof. Suitable modifications include, but are not limited to, interactive surface layers. Examples of interactive surface layers include, but are not limited to, carboxymethyl-dextran hydrogel, alkoxy silanes, and self-assembled monolayers ("SAMs"). In some aspects, a surface can be a biosensor chip.

In some aspects, a surface can be a biorecognition surface. As used herein, the term "biorecognition surface" means a surface comprising a target antigen of interest, e.g., a target antigen bound by a capture agent attached to the surface.

In some aspects, a sample can be applied to a biorecognition surface as a means of phenotyping the sample. The term "sample" as used herein relates to a material or mixture of materials, typically, although not necessarily, in fluid form, e.g., aqueous or in solvent, containing one or more components of interest. Samples can be derived from a variety of sources such as from food stuffs, environmental materials, a biological sample such as tissue or fluid isolated from an individual, including but not limited to, for example, plasma, serum, spinal fluid, semen, lymph fluid, the external sections of the skin, respiratory, intestinal, and genitourinary tracts, tears, saliva, milk, blood cells, tumors, organs, and also samples of in vitro cell culture constituents (including but not limited to conditioned medium resulting from the growth of cells in cell culture medium, putatively virally infected cells, recombinant cells, and cell components). In certain embodiments, a sample can contain an isolated polypeptide, e.g., an antibody, or a plurality of isolated polypeptides, e.g., a plurality of antibodies. In some aspects, a sample is a plasma sample, e.g., a plasma sample treated with caprylic acid (CA). In some aspects, a sample can be a sample that is substantially free of non-IgG proteins and/or von Willebrand factor (vWF). In some aspects, a sample can be a sample that is free of non-IgG proteins and/or von Willebrand factor (vWF) as determined via standard laboratory techniques such as Western blot and/or ELISA.

In some aspects a sample can be from a subject. The term "subject" as used herein includes both humans and non-humans and include but is not limited to mammals, humans, non-human primates, canines, felines, murines, bovines, equines, avians, and porcines. In some aspects, a subject is a mammal. In some aspects, a subject is a human. In some aspects, a subject is a subject having hemophilia A. In some aspects, a subject is a subject having acquired hemophilia A. In some aspects, a subject is a subject having an autoimmune response to Factor VIII. In some aspects, a subject is a patient having hemophilia A or a non-hemophilia A human subject who provided written informed consent, according to the Principles of Helsinki, to participate in a research study.

In some aspects, a sample can include one or more polypeptides, e.g., to be phenotyped via application to a biorecognition surface. The terms "polypeptide" and "protein" are used interchangeably herein. The term "polypeptide" includes polypeptides in which the conventional backbone has been replaced with non-naturally occurring or synthetic backbones and peptides in which one or more of the conventional amino acids have been replaced with one or more non-naturally occurring or synthetic amino acids. It also includes glycopeptides; the sugar moieties may or may not comprise part of the biorecognition surfaces. The term "fusion protein" or grammatical equivalents thereof references a protein composed of a plurality of polypeptide components, that while typically not attached in their native state, typically are joined by their respective amino and carboxyl termini through a peptide linkage to form a single continuous polypeptide. Fusion proteins may be a combination of two, three or even four or more different proteins. The term polypeptide includes fusion proteins, including, but not limited to, fusion proteins with a heterologous amino acid sequence, fusions with heterologous and homologous leader sequences, with or without N-terminal methionine residues; immunologically tagged proteins; fusion proteins with detectable fusion partners, e.g., fusion proteins including as a fusion partner a fluorescent protein, beta-galactosidase, luciferase, albumin, an Fc portion of an antibody, and the like. The phrase "surface-bound polypeptide" refers to a polypeptide that is immobilized on a surface of a substrate. In certain embodiments, the polypeptides employed herein can be present on a surface of the same support, e.g., a sensor.

In some aspects, a polypeptide can be a target antigen. The term "target antigen" refers to a molecule (e.g., a polypeptide, a carbohydrate, or a nucleotide) that includes one or epitopes that can be recognized by immune system components such as antibodies. Typically a target antigen is capable of inducing an immune response in a subject upon administration of the target antigen to the subject in a sufficient amount to induce the immune response. In some aspects, a target antigen is Factor VIII (FVIII) or a portion thereof, e.g., the A2 or C2 domain.

In some aspects, a polypeptide can be a capture agent. The term "capture agent" refers to an agent that binds a target antigen through an interaction that is sufficient to permit the agent to bind and concentrate the target antigen from a homogeneous mixture of different molecules. The binding interaction is typically mediated by an affinity region of the capture agent. Typical capture agents include any moiety that can specifically bind to a target antigen. In certain embodiments, a polypeptide, e.g., an antibody protein, can be employed. Capture agents usually "specifically bind" a target antigen. Accordingly, the term "capture agent" refers to a molecule or a multi-molecular complex which can specifically bind a target antigen with a dissociation constant ($K_D$) of less than about $10^{-6}$ M (e.g., less than about $10^{-7}$ M, less than about $10^{-8}$M, less than about $10^{-9}$M, less than about $10^{-10}$ M, less than about $10^{-11}$ M, less than about $10^{-12}$ M, to about $10^{-16}$ M) without significantly binding to other target antigens. In some aspects, a capture agent is a capture antibody.

In some aspects, an antibody can be used to phenotype a target antigen-specific immune response. Examples of such antibodies include capture antibodies, probe antibodies, and target-antigen specific antibodies from a sample. As used herein, the terms "antibody" and "antibodies" can include, but are not limited to, monoclonal antibodies, multispecific antibodies, human antibodies, humanized antibodies, camelised antibodies, chimeric antibodies, single-chain Fvs (scFv), single chain antibodies, Fab fragments, F(ab') fragments, disulfide-linked Fvs (sdFv), and anti-idiotypic (anti-Id) antibodies (e.g., anti-Id antibodies to antibodies of the disclosure), and epitope-binding fragments of any of the above. In particular, antibodies include immunoglobulin molecules and immunologically active fragments of immunoglobulin molecules (e.g., molecules that contain an antigen binding site). Immunoglobulin molecules can be of any type (e.g., IgG, IgE, IgM, IgD, IgA and IgY), class (e.g., IgG1, IgG2, IgG3, IgG4, IgA1 and IgA2), or subclass. The antibodies can be from any animal origin including birds and mammals (e.g., human, murine, donkey, sheep, rabbit, goat, guinea pig, camel, horse, or chicken). In some aspects, the antibodies are human or humanized monoclonal antibodies. As used herein, "human" antibodies include antibodies having the amino acid sequence of a human immunoglobulin and include antibodies isolated from human immunoglobulin libraries or from mice that express antibodies from human genes. The antibodies can be monospecific, bispecific, trispecific, or of greater multispecificity. Antibodies usually "specifically bind" a target antigen. Accordingly, the term "antibody" refers to a molecule or a multi-molecular complex which can generally specifically bind a target antigen with a dissociation constant ($K_D$) of less than about $10^{-6}$ M (e.g., less than about $10^{-7}$ M, less than about $10^{-8}$ M, less than about $10^{-9}$ M, less than about $10^{-10}$ M, less than about $10^{-11}$ M, less than about $10^{-12}$ M, to about $10^{-16}$ M) without significantly binding to other target antigens. In some aspects, target antigen-specific antibodies from a sample can be anti-Factor VIII (FVIII) antibodies.

The term "antibody/target complex" is a complex that results from the specific binding of an antibody with a target antigen, i.e., a "binding partner pair". An antibody and a target for the antibody will usually specifically bind to each other under "conditions suitable for specific binding", where such conditions are those conditions (in terms of salt concentration, pH, detergent, protein concentration, temperature, etc.) which allow for binding to occur between capture agents and targets to bind in solution. Such conditions, particularly with respect to proteins and antibodies, include those described in Harlow and Lane (Antibodies: A Laboratory Manual Cold Spring Harbor Laboratory, Cold Spring Harbor, N.Y. (1989)) and Ausubel, et al (Short Protocols in Molecular Biology, 5th ed., Wiley & Sons, 2002).

The term "specific binding" refers to the ability of a capture agent and/or antibody to preferentially bind to a particular target antigen that is present in a homogeneous mixture of different target molecules. In certain embodiments, a specific binding interaction will discriminate between desirable and undesirable target antigens in a sample, typically more than about 10 to 100-fold or more (e.g., more than about 1000- or 10,000-fold).

The term "saturation conditions" refers to saturation binding that produces the maximum number of Resonance Units (RU) attainable in a surface plasmon resonance (SPR)-generated sensorgram. Typically, the ligand can be the molecule(s) attached to the SPR biosensor chip (e.g., either covalently or via capture, e.g. by an antibody that is attached covalently to the biosensor chip). The analyte can be the molecule(s) injected over the biosensor chip, and its (their) attachment to the ligand generates a refractive index change, measured as a change in RU on the sensorgram. Saturation binding is appropriate for measuring the maximum amount of analyte captured by the ligand. Thus, saturation binding conditions includes binding conditions representing the maximum binding conditions of a given analyte captured by a ligand (For example, this can be visualized by observing that the binding signal due to the analyte increases rapidly and then reaches a plateau. Longer application times or higher analyte concentrations do not significantly increase the signal further.). In some aspects, the ligand is target antigen-specific antibodies from a sample and the analyte is a probe antibody (e.g., an isotype-specific antibody). The binding of more than one analyte can also be measured in an experiment under saturation conditions. For example, after analyte#1 binds to a ligand, analyte#2 can be injected and the amount of analyte#2 bound to either the ligand or to analyte#1 can be quantified by measuring the change in the sensorgram signal in RUs. In other words, analyte#2 can recognize and bind to a distinct, available recognition surface on either the ligand or on analyte#1. This process can be continued by injecting additional analytes that bind to recognition surfaces not blocked by interactions with the previously injected analytes.

Thus, in some aspects, a biorecognition surface can include a surface contacted with a capture agent, the capture agent can be contacted with a target antigen, the target antigen can be contacted with a plurality of target antigen-specific antibodies from a sample from a subject, and the target-specific antibodies can be contacted with a probe antibody under saturation conditions, e.g., so as to allow a means for determining a phenotype of the target-specific antibodies via a biosensor device such as SPR.

An "array," includes any one-dimensional, two-dimensional or substantially two-dimensional (as well as a three-dimensional) arrangement of addressable regions bearing a particular chemical moiety or moieties (e.g., biopolymers such as polynucleotide or oligonucleotide sequences (nucleic acids), polypeptides (e.g., proteins), carbohydrates, lipids, etc.) associated with that region. In the broadest sense, the arrays are arrays of polymeric binding agents, where the polymeric binding agents may be any of: polypeptides, proteins, nucleic acids, polysaccharides, synthetic mimetics of such biopolymeric binding agents, etc.

Any given substrate (e.g., a surface) can carry one, two, three, four or more arrays disposed on a front surface of the substrate. Depending upon the intended use, any or all of the arrays can be the same or different from one another and each can contain multiple spots or features. A typical array can contain more than ten, more than one hundred, more than one thousand more, more than ten thousand features, or even more than one hundred thousand features, in an area of less than 20 cm$^2$ or even less than 10 cm$^2$. For example, features can have widths (that is, diameter, for a round spot) in the range from a 10 µm to 1.0 cm. In other embodiments each feature can have a width in the range of 1.0 µm to 1.0 mm, usually 5.0 µm to 500 µm, and more usually 10 µm to 200 µm. Non-round features can have area ranges equivalent to that of circular features with the foregoing width (diameter) ranges. At least some, or all, of the features are of different compositions (for example, when any repeats of each feature composition are excluded the remaining features may account for at least 5%, 10%, or 20% of the total number of features). Interfeature areas will typically (but not essentially) be present which do not carry any polynucleotide (or other biopolymer or chemical moiety of a type of which the features are composed). Such interfeature areas typically will be present where the arrays are formed by processes involving drop deposition of reagents but may not be present when, for example, photolithographic array fabrication processes are used. It will be appreciated though, that the interfeature areas, when present, could be of various sizes and configurations.

Each array can cover an area of less than 100 cm², or even less than 50 cm², 10 cm² or 1 cm². In many embodiments, the substrate carrying the one or more arrays may be shaped generally as a rectangular solid (although other shapes are possible), having a length of more than 4 mm and less than 1 m, usually more than 4 mm and less than 600 mm, more usually less than 400 mm; a width of more than 4 mm and less than 1 m, usually less than 500 min and more usually less than 400 mm; and a thickness of more than 0.01 mm and less than 5.0 mm, usually more than 0.1 mm and less than 2 mm and more usually more than 0.2 and less than 1 mm. With arrays that are read by detecting fluorescence, the substrate can be of a material that emits low fluorescence upon illumination with the excitation light. Additionally in this situation, the substrate can be relatively transparent to reduce the absorption of the incident illuminating laser light and subsequent heating if the focused laser beam travels too slowly over a region. For example, a substrate can transmit at least 20%, or 50% (or even at least 70%, 90%, or 95%), of the illuminating light incident on the front as can be measured across the entire integrated spectrum of such illuminating light or alternatively at 532 nm or 633 nm. In embodiments that employ surface plasmon resonance detection, the detected light can have a wavelength in the range of 500 nm to 2000 nm, e.g., 600 nm to 1600 nm or 700 nm to 1250 nm. In particular embodiments, a narrow wavelength or single wavelength of light can be detected.

Arrays can be fabricated using drop deposition from pulse jets of either precursor units (such as amino acid or nucleotide monomers) in the case of in situ fabrication, or the previously obtained polymer. Such methods are described in detail in, for example, the previously cited references including U.S. Pat. No. 6,242,266, U.S. Pat. No. 6,232,072, U.S. Pat. No. 6,180,351, U.S. Pat. No. 6,171,797, U.S. Pat. No. 6,323,043, U.S. patent application Ser. No. 09/302,898 filed Apr. 30, 1999 by Caren et al., and the references cited therein. These references are incorporated herein by reference, in their entirety. Other drop deposition methods can be used for fabrication, as previously described. Also, instead of drop deposition methods, photolithographic array fabrication methods can be used. Interfeature areas need not be present particularly when the arrays are made by photolithographic methods.

An array is "addressable" when it has multiple regions of different moieties (e.g., different polynucleotide sequences) such that a region (i.e., a "feature" or "spot" of the array) at a particular predetermined location (i.e., an "address") on the array will detect a particular target or class of targets (although a feature can incidentally detect non-targets of that feature). Array features are typically, but need not be, separated by intervening spaces. In the case of an array, the "target" will be referenced as a moiety in a mobile phase (typically fluid), to be detected by probes ("target probes") which are bound to the substrate at the various regions. However, either of the "target" or "target probe" can be the one which is to be evaluated by the other (thus, either one could be an unknown mixture of polynucleotides to be evaluated by binding with the other). A "scan region" refers to a contiguous (preferably, rectangular) area in which the array spots or features of interest, as defined above, are found. The scan region is that portion of the total area illuminated from which the resulting fluorescence is detected and recorded. The scan region can include the entire area of the slide scanned in each pass of the lens, between the first feature of interest, and the last feature of interest, even if there exist intervening areas which lack features of interest. An "array layout" refers to one or more characteristics of the features, such as feature positioning on the substrate, one or more feature dimensions, and an indication of a moiety at a given location. "Hybridizing" and "binding", with respect to polynucleotides, are used interchangeably.

If one composition is "bound" to another composition, the compositions do not have to be in direct contact with each other. In other words, bonding can be direct or indirect, and, as such, if two compositions (e.g., a substrate and a polypeptide) are bound to each other, there can be at least one other composition (e.g., another layer) between those compositions. Binding between any two compositions described herein can be covalent or non-covalent. The terms "bound" and "linked" are used interchangeably herein.

The term "sufficient amount" means an amount sufficient to produce a desired effect, e.g., an amount sufficient to modulate protein aggregation in a cell, or an amount sufficient to produce saturation binding conditions in an SPR experiment.

Devices

In some aspects, a device can be used, e.g., to assist in determining a phenotype of a target antigen-specific antibody response. In some aspects the device can be a biosensor device. As used herein, the term "biosensor device" means an analytical device comprising a biorecognition surface. Such a device typically produces a signal in response to a binding interaction at the biorecognition surface. The term includes, but is not limited to, surface plasmon resonance ("SPR") devices. Other devices are described below.

The term "surface plasmon resonance" or "SPR" refers to a detectable electromagnetic phenomenon in which an alteration in a polypeptide can be detected by observing a change in total internal reflectance of a prism coated with a thin metal film.

As used herein, the term "sensorgram" means a plot of response (measured in "resonance units" or "RU") as a function of time. The response corresponds to the amount of material that binds to a sensor surface. An increase of 1000 RU corresponds to an increase of mass on the sensor surface of approximately 1 ng/mm². "$R_{max}$" means the response corresponding to the maximum binding capacity of the sensor surface.

Methods

Also described herein are methods of preparing a surface. In some aspects, a method of producing a prepared surface for use in a biosensor device can include obtaining a biorecognition surface contacted with a plurality of target antigen-specific antibodies from a sample from a subject; and contacting the biorecognition surface with a probe antibody specific for the target antigen-specific antibodies under saturation conditions to produce the prepared surface. In some aspects, the biorecognition surface can include a surface coupled with a capture agent specific for the target antigen, and wherein the target antigen is contacted by the capture agent. In some aspects, obtaining the biorecognition surface can include obtaining a surface, preparing the surface with a capture agent and a target antigen, and then contacting the surface with a plurality of target antigen-specific antibodies from a sample from a subject. In some aspects, obtaining the biorecognition surface can include receiving said surface directly or indirectly from a third party that has contacted the surface with a plurality of target antigen-specific antibodies from a sample from a subject.

Also described herein are methods of antibody response phenotyping. In some aspects, a method for determining the phenotype of a target antigen-specific antibody response in a subject can include contacting a biorecognition surface with a sample from the subject comprising a plurality of target antigen-specific antibodies to produce a contacted surface; contacting the contacted surface with a probe antibody specific for the target antigen-specific antibodies under saturation conditions; and determining, by a biosensor device, the phenotype of the target antigen-specific antibody response in the subject. In some aspects, the phenotype is total target antigen-specific antibody titers; quantitative isotype distribution of the target antigen-specific antibodies; and/or epitope specificity of the target antigen-specific antibodies. In some aspects, the isotype of the quantitative isotype distribution of the target antigen-specific antibodies is selected from the group consisting of IgG, IgG1, IgG2, IgG3, IgG4, IgA, IgM, and IgE. In some aspects, the biorecognition surface comprises a surface coupled with a capture agent specific for the target antigen, and wherein the target antigen is contacted by the capture agent. In some aspects, the method can further include coupling a capture agent specific for the target antigen to a surface and contacting the capture agent with the target antigen to produce the biorecognition surface.

Also described herein is a computer-implemented method for scoring a sample obtained from a subject, wherein the score indicates the phenotype of a target antigen-specific antibody response in the subject, comprising: obtaining, by a biosensor device, a dataset associated with the sample, wherein the sample is obtained from the subject, wherein the dataset comprises target antigen capture level data, capture agent binding level data, and secondary antibody binding level data; and determining, by a computer processor, a score from said dataset using an interpretation function, wherein said score is indicative of the phenotype of the target antigen-specific antibody response in the subject. In some aspects, the method can further include determining, by a computer processor, the phenotype of the target antigen-specific antibody response in the subject, based on said score. In some aspects, the phenotype is total target antigen-specific antibody titers; quantitative isotype distribution of the target antigen-specific antibodies; and/or epitope specificity of the target antigen-specific antibodies. In some aspects, obtaining said dataset associated with said sample comprises obtaining said sample and processing said sample to experimentally determine said dataset. In some aspects, obtaining said dataset associated with said sample comprises receiving said dataset directly or indirectly from a third party that has processed said sample to experimentally determine said dataset.

Also described herein are methods of preparing sample, e.g., for use in phenotyping a target antigen-specific immune response via a biosensor device. In some aspects, a method of preparing a sample for use in a biosensor device can include obtaining the sample, wherein the sample comprises plasma and/or serum from a subject; and contacting the sample with a sufficient amount of caprylic acid (CA) to precipitate non-IgG proteins and von Willebrand factor. In some aspects, the sample can be contacted with sodium acetate. In some aspects, the method can further include removing the precipitate. In some aspects, the method can further include neutralizing the sample before or after the precipitate has been removed, e.g., by contacting the sample with HEPES, sodium chloride, and/or carboxy methyl dextran (CMD).

Pre-analytical treatment of plasma (or serum) samples can be performed using caprylic acid (CA) to precipitate non-IgG proteins and other interfering substances, including von Willebrand factor ("CA treated plasma"). Citrated plasma samples (e.g., 100-500 µL) can be treated by mixing, e.g., 1 part plasma with 2 parts 40 mM sodium acetate pH 4.0 and adding CA to a final concentration of 2.5% v/v. CA concentration can be, e.g., less than 10, 10, 15, 20, 25, 30, 35, 40, 45, 50, 55, 60, 65, 70, 75, 80, or greater than 80 mM (or any integer in between). Other reagents besides sodium acetate, e.g. citric acid/sodium citrate, can be used to buffer the reaction at a similar pH; generally, any buffering agent that buffers in the pH range of about pH 3.0-pH 5.0 can be used. CA can be added to a final concentration of 2.5% v/v, 1.0-4.0% v/v, 2-3% v/v, or 1, 2, 3, or 4% v/v (or any integer between such numbers, e.g., 2.3% v/v). Following incubation with occasional mixing, samples can be centrifuged to pellet the precipitate and filtered. The filtrate can be neutralized, e.g., by adding 1 part to 9 parts 800 mM HEPES pH 8.0, 4M NaCl and 5% CMD. Other reagents besides HEPES, e.g. Trizma base or di- and mono-sodium phosphate, can be used to buffer the reaction at a similar pH. NaCl can be replaced with alternative salts such as KCl and/or $Na_2SO_4$ to increase the ionic strength of the sample to a comparable level. Generally, once the precipitate has been removed, the buffering agent is not critical for the SPR analysis. Ficoll plasma (typically 2-6 fold diluted) can be treated similarly, however initial acidification can be performed by adding 1 part to 9 parts 400 mM sodium acetate pH 4.0 to minimize further dilution. Nominal pre-analytical dilution factors can be calculated for each sample.

SPR measurements can be carried out using a Biacore T-100 instrument (GE Healthcare). Other Biacore instruments can be used (e.g. the Biacore 3000, as well as earlier models and instruments yet to be developed by GE Health Sciences/Biacore or other manufacturers such as Bio-Rad, Octet, Reichert, etc.). Other instruments, in addition to SPR, that register the binding of analytes can be used, e.g., quartz crystal microbalance, ellipsometry, and surface enhanced raman spectroscopy. Capture antibody can be immobilized onto a chip, e.g., a CM5 sensor chip. Any biosensor surface can be used to either attach a ligand covalently, e.g., with an amine-reactive surface, or else noncovalently, e.g., with high affinity. Ligands can be attached covalently using a variety of chemistries. Biacore/GE Healthcare supplies sensor chips compatible with attachment via amine groups, carboxyl groups, thiol groups, carbohydrates, and biotin. For noncovalent attachment, the kinetic off-rate (dissociation rate) is generally slow enough to measure attachment of the analyte(s) before the ligand dissociates from the biosensor surface. Examples of noncovalent attachment surfaces that can be used include: streptavidin chips can be used to attach a biotinylated ligand, or L1 chips can be used to capture a ligand that recognized lipid surfaces.) After immobilizing the capture antibody, the remaining active sites on the sensor chip can be blocked, e.g., by treatment with 1M ethanolamine. A final immobilization signal of 9000 RU can be targeted, if desired.

Binding experiments can be performed in $HBS-P^+$ containing 5 mM $CaCl_2$ ($HBS-P^+/Ca^{2+}$). All injection and binding steps can be performed at a slow flow rate (e.g., 5 µl/min). Target antigen (e.g., 2000-3500 RU) can be captured on the antibody surface by injecting undiluted target antigen. Samples can be injected followed by sequential injections of secondary (isotype-specific) mAbs. Regeneration of the capture surface can be achieved, e.g., with three 20 sec injections of 2M Arginine pH 3.0 at 30 µl/min.

SPR experiments can be carried out under saturation binding conditions for the secondary mAbs to determine the maximum signal from each secondary mAb. This can correspond to stoichiometric binding of the secondary mAbs to the primary IgGs from sample. Quantitative measurements (report points) of target antigen capture level, primary human IgG binding level, and secondary mAb binding levels can be recorded after the end of each sequential injection step.

Singly referenced binding curves can be recorded as the signal from an active flow cell (with captured target antigen) minus the signal from a reference flow cell (without target antigen). Each assay sequence can contain antibody calibrators (e.g., 0, 0.2, 1.0, 2.0, and 5.0 µg/mL in CA-treated inhibitor negative HA plasma). Binding signals can be first normalized to a nominal capture level of target antigen. Calibrators and test samples can typically be tested in blocks of 1, 2, 3, 4, 5, or more injections bracketed by buffer injections. The average binding signals for the bracketing buffer injections can be subtracted from the test sample signals to correct for minor signal variations, e.g., due to incomplete regeneration and/or sensor degradation. Binding signals can be converted from RU to µg/mL Ig using the secondary binding levels of the calibrators. The ratios of the total cumulative secondary mAb binding signal to the primary human antibody binding signal can be calculated.

Computer Implementation

In one embodiment, a computer comprises at least one processor coupled to a chipset. Also coupled to the chipset are a memory, a storage device, a keyboard, a graphics adapter, a pointing device, and a network adapter. A display is coupled to the graphics adapter. In one embodiment, the functionality of the chipset is provided by a memory controller hub and an I/O controller hub. In another embodiment, the memory is coupled directly to the processor instead of the chipset.

The storage device is any device capable of holding data, like a hard drive, compact disk read-only memory (CD-ROM), DVD, or a solid-state memory device. The memory holds instructions and data used by the processor. The pointing device may be a mouse, track ball, or other type of pointing device, and is used in combination with the keyboard to input data into the computer system. The graphics adapter displays images and other information on the display. The network adapter couples the computer system to a local or wide area network.

As is known in the art, a computer can have different and/or other components than those described previously. In addition, the computer can lack certain components. Moreover, the storage device can be local and/or remote from the computer (such as embodied within a storage area network (SAN)).

As is known in the art, the computer is adapted to execute computer program modules for providing functionality described herein. As used herein, the term "module" refers to computer program logic utilized to provide the specified functionality. Thus, a module can be implemented in hardware, firmware, and/or software. In one embodiment, program modules are stored on the storage device, loaded into the memory, and executed by the processor.

Embodiments of the entities described herein can include other and/or different modules than the ones described here. In addition, the functionality attributed to the modules can be performed by other or different modules in other embodiments. Moreover, this description occasionally omits the term "module" for purposes of clarity and convenience.

In some aspects, a system can be used to aid in the determination of an immune response phenotype. In some aspects, a system can include a biorecognition surface comprising a surface contacted with a capture agent, the capture agent contacted with a target antigen, the target antigen contacted with a plurality of target antigen-specific antibodies from a sample from a subject, and the target-specific antibodies contacted with a probe antibody under saturation conditions; and a biosensor device for determining the phenotype of the target antigen-specific antibodies. In some aspects, a system can include a processor for carrying out one or more of the methods disclosed herein.

In some aspects, a computer readable medium can be used to aid in the determination of an immune response phenotype. In some aspects, a computer-readable storage medium storing computer-executable program code, said program code comprising: program code for storing a dataset associated with a sample obtained from a subject, wherein the dataset comprises target antigen capture level data, capture agent binding level data, and secondary antibody binding level data; and program code for analyzing said dataset to determine a score from said dataset using an interpretation function, wherein said score is indicative of the phenotype of a target antigen-specific antibody response in the subject. In some aspects, a computer-readable storage medium storing computer-executable program code can be used for carrying out one or more method disclosed herein.

Kits

Also provided herein are kits, e.g., for determining the phenotype of a target antigen-specific antibody response in a subject. In some aspects, a kit can include a set of reagents comprising a biorecognition surface for determining from a sample obtained from a subject a phenotype of a target antigen-specific antibody response in the subject; and instructions for determining from the sample obtained from the subject the phenotype of the target antigen-specific antibody response in the subject using a biosensor device. Optionally the kit can include packaging. The kit can include reagents and/or instructions for carrying out any of the other types of assays described in this specification. The reagents can be antibodies such as capture antibodies or probe antibodies. In some aspects, a kit can include instructions for coupling a capture agent specific for the target antigen to a surface and contacting the capture agent with the target antigen to produce the biorecognition surface.

It must be noted that, as used in the specification and the appended claims, the singular forms "a," "an" and "the" include plural referents unless the context clearly dictates otherwise.

EXAMPLES

Below are examples of specific embodiments for carrying out the present invention. The examples are offered for illustrative purposes only, and are not intended to limit the scope of the present invention in any way. Efforts have been made to ensure accuracy with respect to numbers used (e.g., amounts, temperatures, etc.), but some experimental error and deviation should, of course, be allowed for.

The practice of the present invention will employ, unless otherwise indicated, conventional methods of protein chemistry, biochemistry, recombinant DNA techniques and pharmacology, within the skill of the art. Such techniques are explained fully in the literature. See, e.g., T. E. Creighton, *Proteins: Structures and Molecular Properties* (W.H. Freeman and Company, 1993); A. L. Lehninger, *Biochemistry* (Worth Publishers, Inc., current addition); Sambrook, et al., *Molecular Cloning: A Laboratory Manual* (2nd Edition, 1989); *Methods In Enzymology* (S. Colowick and N. Kaplan eds., Academic Press, Inc.); *Remington's Pharmaceutical Sciences,* 18th Edition (Easton, Pa.: Mack Publishing Company, 1990); Carey and Sundberg *Advanced Organic Chemistry* 3$^{rd}$ *Ed.* (Plenum Press) Vols A and B (1992).

Materials and Methods.

Reagents

Expired Recombinate™ (Baxter) was reconstituted as directed and used without further manipulation as the source of full-length human Factor VIII (FVIII). Amino-terminally His$_{10}$-tagged FVIII-C2 domain was produced as a soluble cytoplasmic protein in *E. coli* OrigamiB (DE3) pLysS (EMD Chemicals, Gibbstown, N.J.). Caprylic acid, carboxy methyl dextran (CMD), 99.5% L-arginine and other reagents were from Sigma (St. Louis, Mo.). CM5 sensor chips, 1-ethyl-3-(3-dimethylaminopropyl) carbodiimide HCl (EDC), N-hydroxysuccinimide (NHS), ethanolamine, HBS-P+ buffer (10 mM HEPES, 150 mM NaCl, 0.05% (v/v) surfactant P20, pH 7.4) and sodium acetate pH 5.0 were from GE Healthcare (Piscataway, N.J.).

Antibodies

Mouse anti-human FVIII-A1 domain specific mAb (clone GMA-8004) was generously provided by Green Mountain Antibodies. An additional FVIII-C2 domain specific antibody (ESH4) was from American Diagnostica (Stamford, Conn.). Monoclonal anti-huIgG$_1$ (clone HP6188) was obtained from Fitzgerald Industries International (Acton, Mass.). Anti-huIgG$_2$ (clone HP6002), anti huIgG$_3$ (clones HP6050 and HP6047), and anti-huIgG$_4$ (clone HP6023) were from Southern Biotech (Birmingham, Ala.). Anti-huIgA (clone 8203) and anti-huIgM (clone 7408) were from Medix Biochemica (Finland). The human anti-FVIII-C2 mAb B02C11, both the IgG$_4$ and Fab forms, were generously provided by Dr. M. Jacquemin [11]. Antibody concentrations were measured using a nominal extinction coefficient of $\epsilon^{280\ nm, 0.1\%}=1.38$.

Plasma Samples

Blood samples from subjects with hemophilia A (HA) and with autoimmune responses to FVIII (acquired HA) were collected as part of a cross-sectional study (NIH 1RC2HL101851) or were obtained from a Repository maintained by the Pratt laboratory. All subjects provided written informed consent in accordance with the principles of Helsinki Plasma samples from subjects with and without a recently measured inhibitor titer in Bethesda Units (BU)/mL were characterized using the SPR assay. Two types of samples were studied: sodium citrate anti-coagulated plasma (citrated plasma) and diluted heparin-anticoagulated plasma retained following isolation of peripheral blood mononuclear cells (Ficoll plasma). Control experiments to confirm by ELISA assay that caprylic acid (CA) treatment removed all vWF present in human samples also utilized human serum samples.

Pre-Analytical Treatment

Pre-analytical treatment of plasma samples was performed using caprylic acid (CA) to precipitate non-IgG proteins and other interfering substances, including von Willebrand factor and hence baseline circulating FVIII ("CA treated plasma"). Citrated plasma samples (100-500 μL) were treated by mixing 1 part plasma with 2 parts 40 mM sodium acetate pH 4.0 and adding CA to a final concentration of 2.5% v/v. This corresponds to a CA concentration of 50 mM. Following 60 min incubation at room temperature with occasional mixing, samples were centrifuged for 5 minutes at 16,000×g to pellet the precipitate and filtered using a 0.2 mm Spin-X filter (Corning). The transparent filtrate was neutralized by adding 1 part to 9 parts 800 mM HEPES pH 8.0, 4M NaCl and 5% CMD. Ficoll plasma (typically 2-6 fold diluted) was treated similarly, however initial acidification was performed by adding 1 part to 9 parts 400 mM sodium acetate pH 4.0 to minimize further dilution. Nominal pre-analytical dilution factors were calculated for each sample.

SPR Method

SPR measurements were carried out using a Biacore T-100 instrument (GE Healthcare) with binding measurements taken at 25° C. Murine anti-FVIII-A1 (GMA-8004) capture antibody was immobilized covalently onto a CM5 sensor chip from a 100 μg/mL solution in 10 mM sodium acetate pH 5.0 using a mixture of 0.4 M EDC and 0.1 M NHS. After immobilizing the capture antibody, the remaining active sites on the sensor chip were blocked by treatment with 1M ethanolamine. A final immobilization signal of 9000 RU was targeted.

Binding experiments were performed in HBS-P$^+$ containing 5 mM CaCl$_2$ (HBS-P$^+$/Ca$^{2+}$). All injection and binding steps were performed at a slow flow rate (5 μl/min) to minimize FVIII, test plasma and secondary mAb consumption. FVIII (2000-3500 RU) was captured on the GMA 8004 antibody surface by injecting undiluted drug product for 300-600 sec. CA-treated plasma samples were injected for 300 sec followed by sequential 120 sec injections of 25-50 μg/mL secondary (isotype-specific) mAbs. Regeneration of the capture surface was achieved with three 20 sec injections of 2M Arginine pH 3.0 at 30 μl/min. To confirm that CA treatment did not alter the anti-FVIII IgG content of the test plasma, independent samples of untreated inhibitor negative HA plasma containing 1 μg/mL B02C11 (human IgG$_4$) were prepared, CA treated, and the RU signals were compared.

To measure the fraction of the antibody response specific for the FVIII-C2 domain, paired plasma samples from four inhibitor subjects were tested by SPR with and without the addition of increasing concentrations of recombinant FVIII-C2 protein. Plasma samples were diluted first if necessary to bring the total anti-FVIII IgG titer below 5 μg/mL (~33 nM).

Data Analysis

The SPR experiments were carried out under saturation binding conditions for the secondary mAbs to determine the maximum signal from each secondary mAb. Briefly, a sufficiently high concentration of secondary mAb was used so that the binding signal increased rapidly and then reached a plateau within the 2 minute exposure time rather than continuing to increase throughout the exposure. This should correspond to stoichiometric binding of the secondary mAbs to the primary IgGs from plasma. Since the nominal molecular weights of human plasma anti-FVIII IgG and mouse anti-human IgG mAbs are comparable (~150 kDa), the binding signal (RU) for both primary (binding of human anti-FVIII antibodies to the captured FVIII) and secondary (binding of subtype-specific mouse mAbs to human IgG captured from plasma) events should be directly comparable. Quantitative measurements (report points) of FVIII capture level, primary human IgG binding level, and secondary mAb binding levels were recorded 30 sec after the end of each sequential injection step.

Singly referenced binding curves were recorded as the signal from an active flow cell (with captured FVIII) minus the signal from a reference flow cell (without FVIII). Each assay sequence contained mAb B02C11 calibrators (0, 0.2, 1.0, 2.0, and 5.0 μg/mL in CA-treated inhibitor negative HA plasma, see FIG. 1A). Since the FVIII capture level declined slowly over the course of each sequence of samples, and subsequent binding of plasma Abs and secondary mAbs scaled with the FVIII capture level, all binding signals were first normalized to a nominal capture level of 3000 RU FVIII. Calibrators and test samples were typically tested in blocks of 5 injections that were bracketed by buffer injections. The average binding signals for the bracketing buffer injections were subtracted from the test sample signals to correct for minor signal variations due to incomplete regeneration and/or sensor degradation. Binding signals were converted from RU to µg/mL IgG using the secondary binding levels for the BO2C11 calibrators. The ratios of the total cumulative secondary mAb binding signal to the primary human antibody binding signal were also calculated. FIG. 1D depicts a representative binding curve for a plasma sample having a complex antibody phenotype with injection steps and report points annotated.

Example 1: Assay Performance

Acceptable assay performance was typically achieved for 100-150 cycles with a single sensor chip. FVIII capture capacity declined slowly, but this was not typically a limitation. Frequent inclusion of bracketing injections of buffer before and after the injection of plasma samples was undertaken due to a progressive increase in non-sample-specific secondary antibody binding signal. Therefore, subtraction of reference RU values sometimes caused apparent negative referenced binding signals for samples with very low measured RU binding signals, e.g. the % anti-IgG2 signals from several plasma samples (Tables 1-3). If the response (in RUs) of bracketing buffer injections was reproducible, sample signals were corrected by subtracting the mean signals from the bracketing buffer injections. If not, samples were retested using a new sensor chip.

The use of affinity-captured FVIII antigen placed limits on the dynamic range of quantitative measurements. Although normalized calibration curves using the patient-derived inhibitory antibody BO2C11 were highly reproducible across multiple days and sensors (FIG. 1A) the dynamic range for the SPR assay was narrow, with a range of quantification from 0.2 µg/ml (~1 nM) to 5 µg/ml (~33 nM). Below 0.2 µg/ml, signal to noise ratios were too low to obtain reliable information. BO2C11 binds to FVIII with an apparent dissociation constant $K_D \sim 2 \times 10^{-11}$ mol $L^{-1}$ and inhibits its pro-coagulant activity with a specific activity of ~7,000 BU/mg [11]; these spike-recovery assays indicated the lower limit for detection of this high-affinity neutralizing antibody by SPR was 0.2 µg/ml~1.4 BU/ml. Above 5 µg/ml, accurate concentration measurements could not be obtained due to saturation of the affinity-captured FVIII, but the IgG subtype distribution could still be measured. The spike-recovery experiment with 1.0 µg/ml (~7 nM) BO2C11 demonstrated a recovery of 109±16% (FIG. 1B). As expected for BO2C11 (human $IgG_4$), this response was $IgG_4$-restricted and the ratio of secondary ($IgG_1+IgG_2+IgG_3+IgG_4$ signals) to primary (polyclonal anti-FVIII antibodies) binding RU signals was close to stoichiometric (94±10%). In addition to satisfactory recovery of BO2C11 following CA treatment, the behavior of independently treated and tested samples from a given subject, including both citrated plasma and Ficoll-treated heparin-anticoagulated plasma, was reproducible when assayed using different sensors and with different sample preparations. Once treated with CA, the samples remained stable for several weeks at 4° C. The dynamic range of the SPR assay was from 0.2-33 µg/ml anti-FVIII antibody, corresponding to ~1.4-35 BU/ml for the high-affinity neutralizing monoclonal antibody BO2C11 (FIG. 1A). Subject Q-012 had an initial inhibitor titer of 2 BU/ml and the corresponding anti-FVIII antibody titer by SPR was ~6.4 µg/ml (Table 2), indicating that an inhibitor titer of ~0.3 BU/ml could be detected in this polyclonal IgG sample.

SPR of four plasma samples incubated with different concentrations of FVIII-C2 showed that in all cases, the competitive response (recombinant FVIII-C2 displacing FVIII-C2-specific antibodies) was saturated by >100 nM FVIII-C2 (FIG. 1C). FIG. 1D depicts a representative binding curve for a plasma sample having a complex antibody phenotype with injection steps and report points annotated.

The assay format described herein is suitable for measurement of small (50-100 µL) volumes (e.g. residual samples from clinical assays) and for high to medium-throughput analysis of multiple samples.

Example 2: HA Phenotypes

Figure 2:
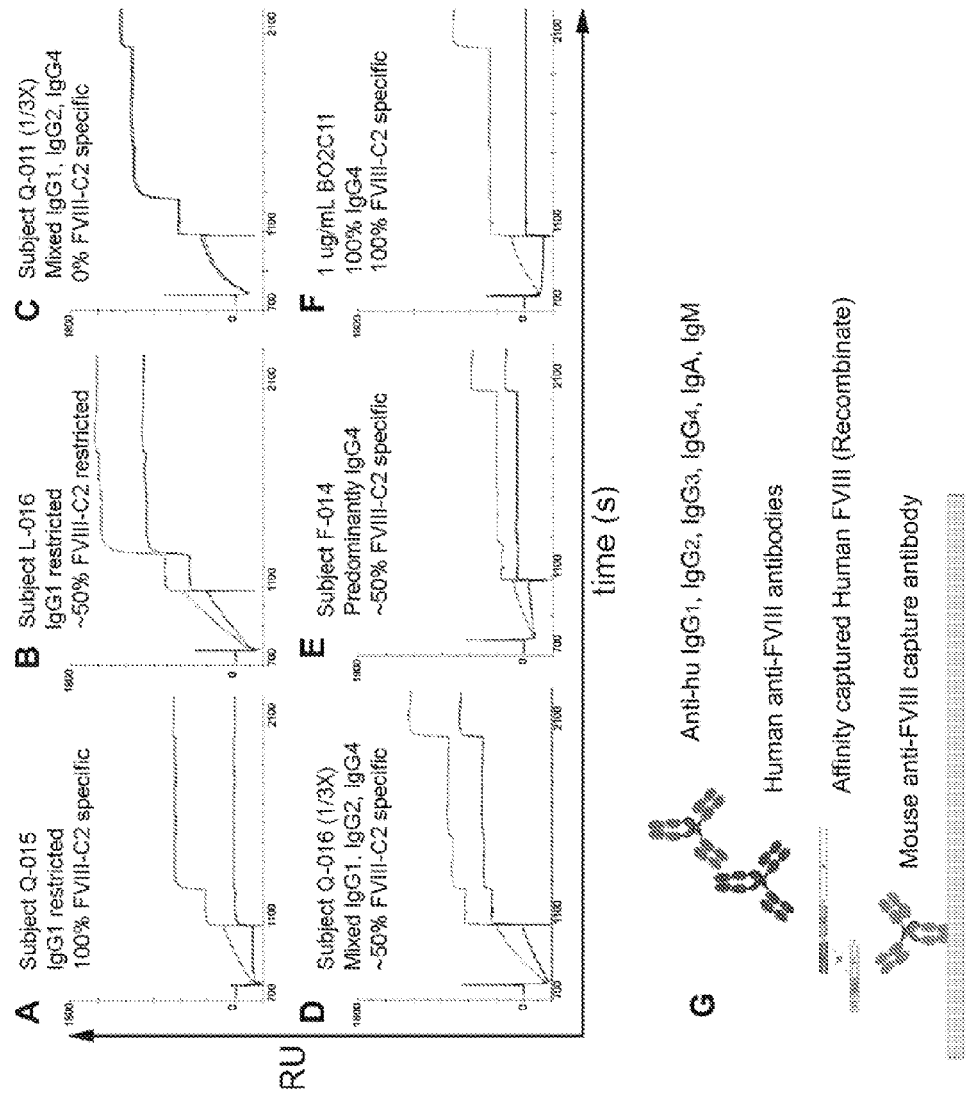
FIG. 2: (A)-(F): Binding curves from matched plasma samples with and without the addition of saturating (1 µM) recombinant FVIII-C2; G) One embodiment of the biosensor assay format is shown schematically.

Representative binding curves illustrating the range of phenotypic responses are shown in FIG. 2. Each panel shows binding curves obtained in the presence and absence of excess (1 µM) FVIII-C2. Quantitative measurements (percent of the response derived from each human IgG subtype, total anti-FVIII IgG concentration (µg/mL), and the ratio of secondary to primary binding signal in %) obtained from the binding curves were tabulated in Tables 1&2. Almost every permutation (IgG subtype distribution, proportion of FVIII-C2 specific antibodies, and anti-FVIII IgG concentration) of phenotypic response was observed. Two subjects (B-002 and Q-011) demonstrated a complete lack of competition with FVIII-C2, whereas anti-FVIII antibodies in samples from subject Q-015 were completely specific for FVIII-C2. However, the most common response was a mixed IgG subtype distribution with 40-80% FVIII-C2 specificity. For both the cross-sectional, single time point samples and the serial samples, no significant divergence between the total IgG subtype distribution and the FVIII-C2-specific IgG subtype distribution was observed. Three HA subjects (Q-015, N-008 and L-006) exhibited a predominantly $IgG_1$ restricted response. Another three HA subjects (F-014, B-002 and A-002) exhibited predominantly $IgG_4$-restricted responses, however detectable levels of other IgG subtypes were also observed. Samples from the four autoimmune HA subjects (Q-011, Q-012, Q-016 and Q 033) all exhibited complex mixtures of $IgG_1$, $IgG_2$ and $IgG_4$ in addition to high total anti-FVIII IgG concentrations. In addition to testing with IgG subtype-specific secondary antibodies, the samples were screened with anti-IgA and anti-IgM secondary antibodies (data not shown). No samples in this study exhibited an IgA or IgM response; however positive controls indicated that the system was capable of detecting these non-IgG forms of antibody response.

Serial samples were obtained from two of the autoimmune HA subjects (Q-011 and Q-012) and from two congenital HA subjects (L-006 and Q-015) following initial presentation with an inhibitor. For samples from subjects Q-011 and Q-012 (Table 2), a progressive decrease in total anti-FVIII IgG concentrations was observed, with levels becoming undetectable six months after inhibitor diagnosis for Q-012. For the serial samples from moderate HA subject L-006, trace levels of $IgG_3$ were observed in the earliest sample, and trace $IgG_4$ was found in samples obtained one and two months later. Rituximab therapy subsequently resulted in a predictable decrease in his anti-FVIII IgG concentrations. For mild HA subject Q-015, the response was $IgG_1$-restricted throughout the first year following initial inhibitor detection, but a low-titer sample obtained 5 years later, during which time he received several additional FVIII infusions following a traumatic injury, showed partial $IgG_4$ character. SPR measurements of a sample obtained from this subject 1-3 weeks after initial inhibitor detection indicated that ~30% of the anti-FVIII antibodies bound to the FVIII C2 domain (estimated from RUs measured in the presence of saturating FVIII-C2 protein, Table 2) and samples obtained later in the course of this immune response exhibited nearly complete specificity for the C2 domain.

The analysis of serial samples from subjects with an allo- or auto-immune response to FVIII by SPR presents a method that will be applicable to future prospective studies of inhibitor development, given the small sample size requirement and the demonstrated ability to follow dynamic changes in antibody titers, subtypes and FVIII domain specificity. Table 3 summarizes demographic and HA-related clinical information regarding the inhibitor-positive subjects.

The SPR method described herein is an easily adaptable assay format with which to characterize anti-target antibody responses, e.g., anti-FVIII antibody responses. The assay sensitivity is satisfactory to characterize inhibitors detectable using the Bethesda assay and its reproducibility, particularly with respect to characterizing the IgG subtype distribution and FVIII-C2 domain specificity, is excellent. Several observations were notable: As has already been reported, the $IgG_4$ subtype was commonly observed, typically in mixed subtype responses. However, three HA subjects with inhibitor responses (2 emerging, 1 chronic) demonstrated $IgG_1$-restricted responses. Also, most subjects exhibited partial FVIII-C2 specificity (40-80% of the anti-FVIII antibodies). Autoimmune subjects exhibited complex responses involving multiple IgG subtypes, multiple domain specificities, high total anti-FVIII antibody concentrations, and an apparently high ratio of total to inhibitory anti FVIII IgG. The present study analyzed plasma samples from 22 inhibitor subjects, including serial samples from two HA subjects with a recently diagnosed inhibitor and two acquired HA subjects following initial detection of their autoimmune response to FVIII. The platform described herein is a promising approach to carry out future prospective studies of FVIII inhibitors and other ADA antibody responses. Because of the small plasma volumes used and the quick assay turnaround time, this method is especially suitable for batch analysis of multiple samples, e.g., central laboratory characterization of ADA responses to FVIII or other clinically important antigens.

Example 3: Serum Samples

In some circumstances, e.g., in which only anti-drug antibodies are of interest, blood samples are allowed to clot and the resulting serum is collected. Other serum collection methods are generally known in the art. Although coagulation proteins, such as fibrinogen, are depleted in serum, it still contains most of the same blood components found in plasma that can interfere with binding measurements such as those described above. Pre-analytical treatment of serum with CA renders it suitable for the same sample analysis as the CA treated plasma samples described above. Serum is treated in the same way with the same proportions of reagents as those described for plasma. ELISA assays confirms that CA treatment of serum as well as plasma reduced the vWF content of the sample to below detectable levels.

The materials and methods described above are carried out as described above with serum samples, rather than plasma samples. Similar results are obtained.

Example 4: CA-Treated Sample Characterization

The following experiment was performed to determine whether caprylic acid (CA) treatment removes or significantly reduces VWF in plasma and serum samples.

Plasma and serum samples: All subjects provide written informed consent, in accordance with the Principles of Helsinki Blood samples were drawn by a research nurse at the Puget Sound Blood Center Research Institute. Five samples were used. See Table 4. For each sample a dilution series was run to compare untreated samples with CA-treated samples. Untreated samples were diluted to the same extent as the CA-treated samples prior to preparing the dilution curves. A standard curve was also run with purified VWF.

Pre-analytical treatment of plasma or serum samples was performed using caprylic acid (CA) to precipitate non-IgG proteins and other interfering substances, including vWF and hence baseline circulating FVIII ("CA treated plasma"). ELISA assays were carried out for a representative subset of samples (Table 4) to ascertain whether CA treatment indeed removed all residual vWF. Citrated plasma or serum samples (100 μL) were treated by mixing 1 part plasma with 2 parts 40 mM sodium acetate pH 4.0 and adding CA to a final concentration of 2.5% v/v (158 mM). Following 60 min incubation at room temperature with occasional mixing, samples were centrifuged for 5 min at 16,000×g to pellet the precipitate and filtered using a 0.2 mm Spin-X filter (Corning). The transparent filtrate was neutralized by adding 1 part (200 μl) to 9 parts 800 mM HEPES pH 8.0, 4M NaCl and 5% CMD (1800 μl). Total sample dilution was 30×. Untreated and CA treated samples were stored overnight at 4° C. VWF ELISA assays were carried out the following day.

Human VWF ELISA assays were then performed using standard procedures. The following reagents and devices were used:

Polyclonal rabbit anti-human Von Willebrand Factor Code A0082, Dako (Code A0082), Lot 0075602.

Human von Willebrand Factor (VIII Free) (Haemoatologic Technologies Inc., HCVWF-0191). Lot BB0418.

Peroxidase-conjugated rabbit anti-human Von Willebrand Factor Code P0226, 1.3 g/L (Dako, Code P0226). Lot 00073780.

SoftMax Pro 5.2 Molecular Devices SpectraMax M5 ELISA plate reader.

Coating Buffer (0.01 M Phosphate buffer, 0.15 M NaCl, pH 7.2).

10× DPBS, no Ca and Mg (26.67 mM KCl, 14.71 mM $KH_2PO_4$, 1379.31 mM NaCl, 80.6 mM $Na_2HPO_4$-$7H_2O$).

1× DPBS Wash buffer w/o Ca (1× PBS, 0.05% TWEEN™ 20).

5× assay diluent (eBioscience, 00-4202).

Dilution Buffer (20 mM HEPES, 150 mM NaCl, 0.05% TWEEN™ 80, pH 7.4).

Super AquaBlue ELISA substrate (eBiosciences, 00-4203).

Polyclonal rabbit anti-human vWF Code A0082 (Dako, Carpinteria, Calif.) was diluted to 1 μg/ml in 0.01 M phosphate buffer, 0.15 M NaCl, pH 7.2. Diluted antibody (100 μl) was added to each well of a NUNC Maxisorp 96 ELISA plates and incubated overnight at 4° C. Plates were than washed 5× in 300 μl 1×D-PBS containing 0.05% TWEEN™ 20 (wash buffer). Blocking buffer was prepared by diluting 5× assay diluent (eBiosciences, San Diego, Calif.) to 1× in MilliQ water. Blocking Buffer, 200 μl per well was added, and the plates were incubated for 3 hrs at room temperature. Serial dilutions (2× to 64×) into 20 mM HEPES, 150 mM NaCl, 0.05% TWEEN™ 80, pH 7.4 (Dilution Buffer) of untreated and CA treated plasma/serum samples were prepared. Untreated plasma samples were first diluted 30× to match the dilution of CA treatment prior to serial dilutions. Serial dilutions of purified vWF FVIII free (Haematologic Technologies Inc., Burlington, Vt.) (15.6-1000 ng/ml) were prepared as an internal standard. Plates were than washed 5× in wash buffer, 100 µl samples and standards were added to the plate and incubated for 2 hrs at room temperature. Plates were than washed 5× in wash buffer, peroxidase-conjugated rabbit anti-human vWF Code P0226 (Dako) was diluted 1:8000 in Dilution Buffer and 100 µl was added to each well and incubated for 1 hr at room temperature. Wells were washed 5× in Wash Buffer, 100 µl of Super Aquablue ELISA substrate (eBiosciences) was added to each well, and $A_{405}$ was read on a Molecular Devices SpectraMax M5 ELISA plate reader. The amount of vWF in the plasma/serum samples was extrapolated from the standard curve using SoftMax Pro 5.2 software.

Figure 3:
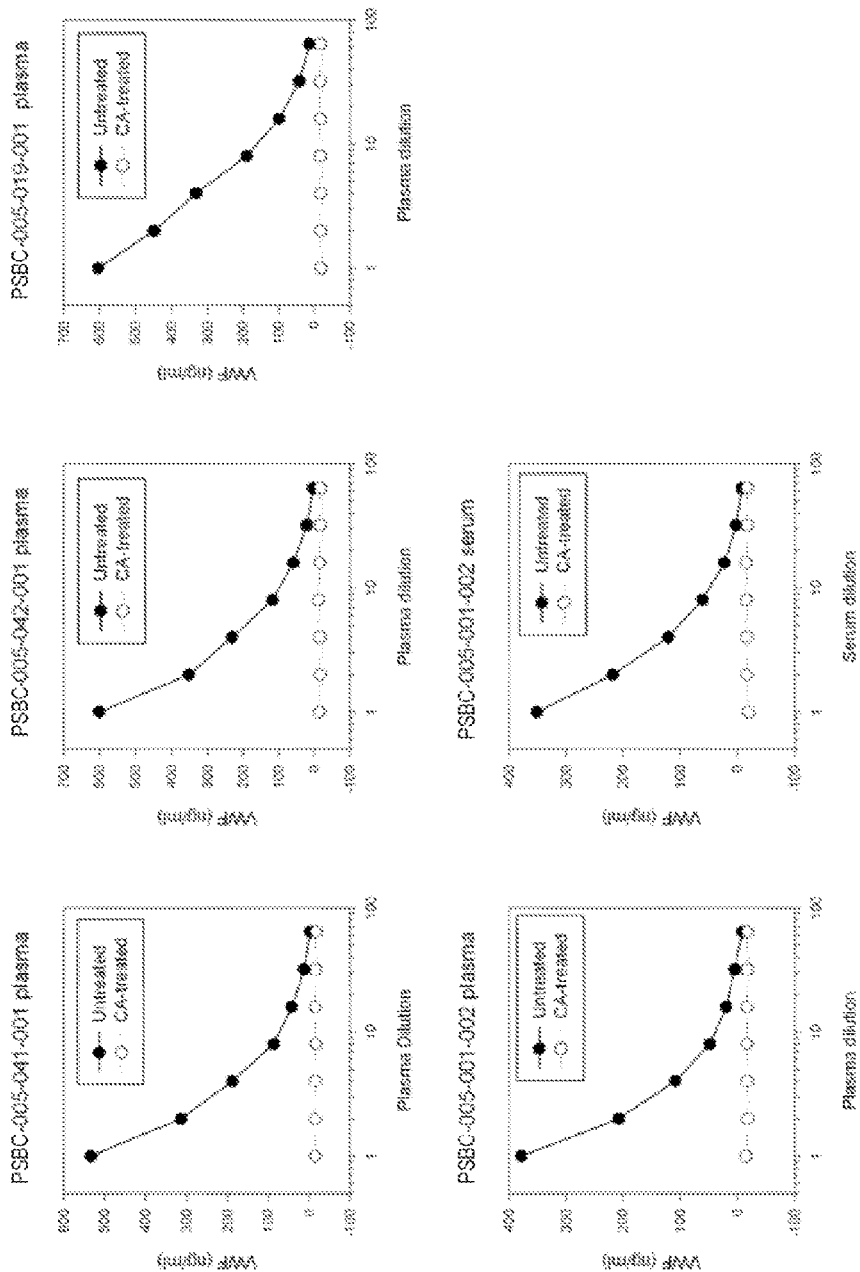
FIG. 3 shows each sample plotted on a separate graph comparing untreated sample with CA-treated sample. The plotted $A_{405}$ reading was taken after 20 minutes of color development.
Figure 4:
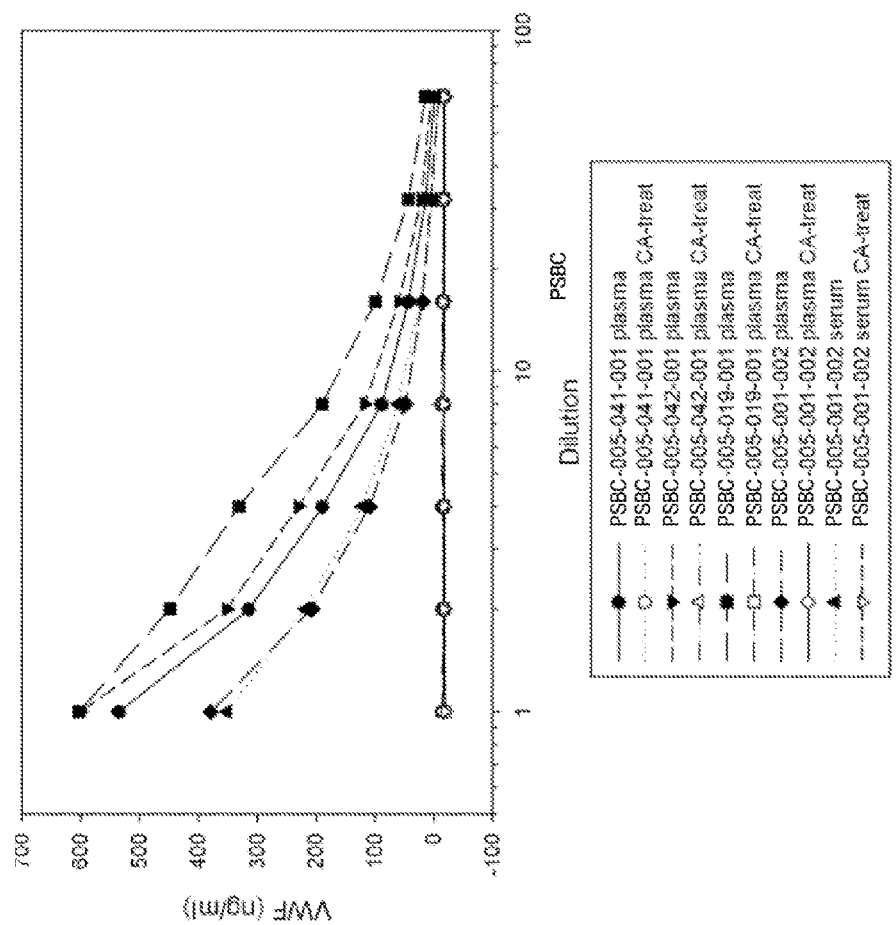
FIG. 4 shows an overlay of the individual graphs shown in FIG. 3.

FIG. 3 shows each sample plotted on a separate graph comparing untreated sample with CA-treated sample. The plotted $A_{405}$ reading was taken after 20 minutes of color development. FIG. 4 shows an overlay of the individual graphs shown in FIG. 3.

VWF was undetectable in samples precipitated with CA. This was found for normal citrated plasma, severe hemophilia A citrated plasma, normal serum, and for both fresh and frozen samples. Thus, CA treatment of a sample (e.g., a plasma or serum sample taken from a subject) results in a CA-treated sample that is substantially free of VWF.

While the invention has been particularly shown and described with reference to a preferred embodiment and various alternate embodiments, it will be understood by persons skilled in the relevant art that various changes in form and details can be made therein without departing from the spirit and scope of the invention.

All references, issued patents and patent applications cited within the body of the instant specification are hereby incorporated by reference in their entirety, for all purposes.

REFERENCES

1. Ehrenforth S, Kreuz W, Scharrer I, Linde R, Funk M, et al. (1992) Incidence of development of factor VIII and factor IX inhibitors in haemophiliacs. Lancet 339: 594-598.
2. Kasper C K, Aledort L, Aronson D, Counts R, Edson J R et al. (1975) Proceedings: A more uniform measurement of factor VIII inhibitors. Thromb Diath Haemorrh 34:612.
3. Verbruggen B, Novakova I, Wessels H, Boezeman J, van den Berg M, Mauser-Bunschoten E (1995) The Nijmegen modification of the Bethesda assay for factor VIII:C inhibitors: improved specificity and reliability. Thromb Haemost 73: 247-251.
4. Sahud M A, Pratt K P, Zhukov O, Qu K, Thompson A R (2007) ELISA system for detection of immune responses to FVIII: a study of 246 samples and correlation with the Bethesda assay. Haemophilia 13: 317-322.
5. Zakarija A, Harris S, Rademaker A W, Brewer J, Krudysz-Amblo, et al. (2011) Alloantibodies to factor VIII in haemophilia. Haemophilia 17: 636-640.
6. Krudysz-Amblo J, Parhami-Seren B, Butenas S, Brummel-Ziedens K E, Gomperts E D, et al. (2009) Quantitation of anti-factor VIII antibodies in human plasma. Blood 113: 2587-2594.
7. Towfighi F, Gharagozlou S, Sharifian R A, Kazemnejad A, Esmailzadeh K, et al. (2005) Comparative measurement of anti factor VIII antibody by Bethesda assay and ELISA reveals restricted isotype profile and epitope specificity. Acta Haematol 114: 84-90.
8. Shetty S, Ghosh K, Mohanty D (2003) An ELISA assay for the detection of factor VIII antibodies-comparison with the conventional Bethesda assay in a large cohort of haemophilia samples. Acta Haematol 109: 18-22.
9. Irigoyen M B, Primiani L, Felippo M, Candela M, Bianco R P, et al. (2011) A flow cytometry evaluation of anti-FVIII antibodies: correlation with ELISA and Bethesda assay. Haemophilia 17: 267-274.
10. Pratt K P, Thompson A R (2009) B-Cell and T-Cell epitopes in anti-factor VIII immune responses. Clin Rev Allergy Immunol 37: 80-95.
11. Jacquemin M G, Desqueper B G, Benhida A, Vander Elst L, Hoylaerts M F, et al. (1998) Mechanism and kinetics of factor VIII inactivation: study with an $IgG_4$ monoclonal antibody derived from a hemophilia A patient with inhibitor. Blood 92: 496-506.
12. Fulcher C A, de Graaf Mahoney S, Zimmerman T S (1987) FVIII inhibitor IgG subclass and FVIII polypeptide specificity determined by immunoblotting. Blood 69: 1475-1480.
13. van Helden P M, van den Berg H M, Gouw S C, Kaijen P H, Zuurveld M G, et al. (2008) IgG subclasses of anti-FVIII antibodies during immune tolerance induction in patients with hemophilia A. Br J Haematol 142: 644-652.
14. Aalberse R C, van der Gaag R, van Leeuwen J. (1983) Serologic aspects of $IgG_4$ antibodies. I. Prolonged immunization results in an $IgG_4$-restricted response. J Immunol 130: 722-726.
15. Scandella D, Mattingly M, de Graaf S, Fulcher C A (1989) Localization of epitopes for human factor VIII inhibitor antibodies by immunoblotting and antibody neutralization. Blood 74: 1618-1626.
16. Fulcher C A, Lechner K, de Graaf Mahoney S (1988) Immunoblot analysis shows changes in factor VIII inhibitor chain specificity in factor VIII inhibitor patients over time. Blood 72: 1348-1356.
17. Prescott R, Nakai H, Saenko E L, Scharrer I, Nilsson I M, et al. (1997) The inhibitor antibody response is more complex in hemophilia A patients than in most nonhemophiliacs with factor VIII autoantibodies. Recombinate and Kogenate Study Groups. Blood 89: 3663-3671.
18. Scandella D, Gilbert G E, Shima M, Nakai H, Eagleson C, et al. (1995) Some factor VIII inhibitor antibodies recognize a common epitope corresponding to C2 domain amino acids 2248 through 2312, which overlap a phospholipid-binding site. Blood 86: 1811-1819.
19. Reding M T, Lei S, Lei H, Green D, Gill J, Conti-Fine B M (2002) Distribution of Th1- and Th2-induced anti-factor VIII IgG subclasses in congenital and acquired hemophilia patients. Thromb Haemost 88: 568-575.
20. Sánchez-Cuenca J M, Carmona E, Villanueva M J, Aznar J A (1990) Immunological characterization of factor VIII inhibitors by a sensitive micro-ELISA method. Thromb Res 57: 897-908.
21. Lollar P, Hill-Eubanks D C, Parker C G (1988) Association of the factor VIII light chain with von Willebrand factor. J Biol Chem 263: 10451-10455.
22. Ling M, Duncan E M, Rodgers S E, Street M, Lloyd J V (2001) Classification of the kinetics of factor VIII inhibitors in haemophilia A: plasma dilution studies are more discriminatory than time-course studies. Br J Haematol 114: 861-867.
23. Grancha S, Ortiz A A, Maranon C, Hampel K, Moret A, et al. (2012) Kinetics of the interaction between anti-FVIII antibodies and FVIII from therapeutic concentrates, with and without von Willebrand factor, assessed by surface plasmon resonance. Haemophilia (epub ahead of print).

24. Parkkinen J, Rahola A, von Bonsdorff L, Tölö H, Törmä E (2006) A modified caprylic acid method for manufacturing immunoglobulin G from human plasma with high yield and efficient virus clearance. Vox Sang 90: 97-104.
25. Bergmann-Leitner E S, Mease R M, Duncan E H, Khan F, Waitumbi J, Angov E (2008) Evaluation of immunoglobulin purification methods and their impact on quality and yield of antigen-specific antibodies. Malar J 7: 129.
26. Ejima D, Yumioka R, Tsumoto K, Arakawa T (2005) Effective elution of antibodies by arginine and arginine derivatives in affinity column chromatography. Anal Biochem. 345: 250-257.
27. Gibbs E, Oger J (2008) A biosensor-based characterization of the affinity maturation of the immune response against interferon-beta and correlations with neutralizing antibodies in treated multiple sclerosis patients. J Interferon Cytokine Res 28: 713-723.
28. Narita M, Yamada S, Matsuzono Y, Itakura O, Togashi T, Kikuta H (1997) Measles virus-specific immunoglobulin G subclass response in serum and cerebrospinal fluid. Clin Diagn Virol 8: 233-239.
29. Hamilton R G, Morrison S L (1993) Epitope mapping of human immunoglobulin-specific murine monoclonal antibodies with domain-switched, deleted and point-mutated chimeric antibodies. J Immunol Methods 158: 107-122.
30. Jackola D R, Pierson-Mullany L K, Liebeler C L, Blumenthal M N, Rosenberg A (2002) Variable binding affinities for allergen suggest a 'selective competition' among immunoglobulins in atopic and non-atopic humans. Mol Immunol 39: 367-377.
31. Karlsson R, Fägerstam L, Nilshans H, Persson B (1993) Analysis of active antibody concentration. Separation of affinity and concentration parameters. J Immunol Methods 166: 75-84.
32. van Remoortere A, van Dam G J, Hokke C H, van den Eijnden D H, van Die I, et al. (2001) Profiles of immunoglobulin M (IgM) and IgG antibodies against defined carbohydrate epitopes in sera of Schistosoma-infected individuals determined by surface plasmon resonance. Infect Immun 69: 2396-23401.
33. Gouw S C, van der Bom J G, Auerswald G, Ettinghausen C E, Tedgard U, van den Berg H M (2007) Recombinant versus plasma-derived FVIII products and the development of inhibitors in previously untreated patients with severe hemophilia A: the CANAL cohort study. Blood 109: 4693-4697.
34. Gilles J G, Arnout J, Vermylen J, Saint-Remy J M (1993) Anti-factor VIII antibodies of hemophiliac patients are frequently directed towards nonfunctional determinants and do not exhibit isotypic restriction. Blood 82: 2452-2461.
35. Meeks S L, Healey J F, Parker E T, Barrow R T, Lollar P (2008) Nonclassical anti-C2 domain antibodies are present in patients with factor VIII inhibitors. Blood 112:1151-1153.
36. Meeks S L, Healey J F, Parker E T, Barrow R T, Lollar P (2007) Antihuman factor VIII C2 domain antibodies in hemophilia A mice recognize a functionally complex continuous spectrum of epitopes dominated by inhibitors of factor VIII activation. Blood 110: 4234-4242.
37. Lollar P (1997) Analysis of factor VIII inhibitors using hybrid human/porcine factor VIII. Thromb Haemostas 78: 647-651.
38. Barrow R T, Healey J F, Gailani D, Scandella D, Lollar P (2000) Reduction of the antigenicity of factor VIII toward complex inhibitory antibody plasmas using multiply-substituted hybrid human/porcine factor VIII molecules. Blood 95: 564-568.
39. Kessel C, Königs C, Linde R, Excuriola-Ettinghausen C, Stoll H, et al. (2008) Humoral immune responsiveness to a defined epitope on factor VIII before and after B cell ablation with rituximab. Mol Immunol 46: 8-15.
40. Raut S, Villard S, Grailly S, Gilles J G, Granier C, et al. (2003) Anti-heavy-chain monoclonal antibodies directed to the acidic regions of the factor VIII molecule inhibit the binding of factor VIII to phospholipids and von Willebrand factor. Thromb Haemost 90: 385-397.
41. Kopecky E M, Greinstetter S, Pabinger I, Buchacher A, Römisch J, Jungbauer A (2006) Mapping of FVIII inhibitor epitopes using cellulose-bound synthetic peptide arrays. J Immunol Methods 308: 90-100.
42. Albert T, Egler C, Jakuschev S, Schuldenzucker U, Schmitt A, et al. (2008) The B-cell epitope of the monoclonal anti-factor VIII antibody ESH8 characterized by peptide array analysis. Thromb Haemost 99: 634-637.
43. Lavigne-Lissalde G, Tarrade C, Lapalud P, Chtourou S, Schved J F, et al. (2008) Simultaneous detection and epitope mapping of anti-factor VIII antibodies. Thromb Haemost 99: 1090-1096.
44. van der Neut Kolfschoten M, Schuurman J, Losen M, Bleeker W K, Martinez-Martinez P, et al. (2007) Anti-inflammatory activity of human $IgG_4$ antibodies by dynamic Fab arm exchange. Science 317: 1554-1557.
45. Lewis K B, Meengs B, Bondensgaard K, Chin L, Hughes S D, et al. (2009) Comparison of the ability of wild type and stabilized human $IgG_4$ to undergo Fab arm exchange with endogenous $IgG_4$ in vitro and in vivo. Mol Immunol 46: 3488-3494.
46. Labrijn A F, Buijsse A O, van den Bremer E T, Verwilligen A Y, Bleeker W K, et al. (2009) Therapeutic $IgG_4$ antibodies engage in Fab-arm exchange with endogenous human $IgG_4$ in vivo. Nat Biotechnol 27: 767-771.

TABLES

TABLE 1

| Subject | IgG1 + 2 + 3 + 4 (RU)/ polyclonal IgG (RU) | % $IgG_1$ | % $IgG_2$ | % $IgG_3$ | % $IgG_4$ | Total anti-FVIII IgG from SPR (μg/ml) |
|---|---|---|---|---|---|---|
| Antibody subtypes and estimated titers by SPR | | | | | | |
| Predominantly $IgG_1$ Response | | | | | | |
| Q-015 (n = 2) | 1.11(2%) | 95%(2%) | 0%(1%) | −1%(0%) | 5%(1%) | 3.11(0.62) |
| Q-015 + FVIII-C2 | ND* | ND | ND | ND | ND | <0.2 |
| N-008 | 0.98 | 104% | −6% | 1% | 1% | 5.45 |
| N-008 + FVIII-C2 | 1.01 | 106% | −10% | 3% | 0% | 2.4 |
| L-006-001 | 0.87 | 92% | 4% | 4% | 0% | 11.85 |
| L-006-001 + FVIII-C2 | 0.83 | 88% | 7% | 5% | −1% | 4.89 |

TABLE 1-continued

Antibody subtypes and estimated titers by SPR

| Subject | IgG1 + 2 + 3 + 4 (RU)/ polyclonal IgG (RU) | % IgG$_1$ | % IgG$_2$ | % IgG$_3$ | % IgG$_4$ | Total anti-FVIII IgG from SPR (µg/ml) |
|---|---|---|---|---|---|---|
| Predominantly IgG$_4$ Response | | | | | | |
| F-014 (n = 2) | 1.26(7%) | 16%(1%) | −1%(0%) | 0%(1%) | 85%(1%) | 2.67(0.53) |
| F-014 + FVIII-C2 (n = 2) | 1.49(13%) | 14%(1%) | −17%(0%) | 2%(2%) | 101%(3%) | 1.09(0.18) |
| B-002 | 1.24 | 8% | 7% | −1% | 86% | 2.42 |
| B-002 + FVIII-C2 | 1.26 | 7% | 7% | −1% | 86% | 2.38 |
| A-002 | 1.16 | 4% | 5% | −1% | 92% | 4.38 |
| A-002 + FVIII-C2 | 1.24 | 1% | 7% | −1% | 93% | 2.57 |
| Mixed IgG Subtype Response | | | | | | |
| G-004 | 1.13 | 43% | −4% | −1% | 62% | 9.1 |
| G-004 + FVIII-C2 | 1.25 | 42% | −10% | −1% | 69% | 5.11 |
| C-010 | 0.81 | 80% | −3% | −2% | 25% | 1.59 |
| C-010 + FVIII-C2 | 0.82 | 55% | −3% | −2% | 50% | 0.9 |
| D-006 (n = 3) | 2.04(48%) | 45%(3%) | −6%(7%) | 1%(1%) | 61%(3%) | 1.53(0.41) |
| D-006 + FVIII-C2 | ND | ND | ND | ND | ND | <0.2 |
| L-025 | 1.12 | 72% | 1% | −1% | 28% | 3.56 |
| L-025 + FVIII-C2 | 1.15 | 64% | 3% | −1% | 34% | 2.17 |
| P-011 | 1.18 | 38% | 1% | −1% | 61% | 18.29 |
| P-011 + FVIII-C2 | 1.20 | 29% | −1% | −1% | 73% | 11.28 |
| P-001 | 0.98 | 23% | 3% | 0% | 75% | 22.58 |
| P-001 + FVIII-C2 | 1.02 | 34% | 4% | −1% | 63% | 3.97 |
| F-006 | 1.01 | 31% | 8% | −2% | 62% | 24.94 |
| F-006 + FVIII-C2 | 1.19 | 42% | 6% | −2% | 54% | 6.46 |
| A-008 | 1.09 | 41% | 11% | −1% | 49% | 3.78 |
| A-008 + FVIII-C2 | 1.12 | 36% | 11% | −1% | 54% | 2.02 |
| F-025 (n = 2) | 2.19(51%) | 30%(1%) | 22%(4%) | −1%(0%) | 50%(3%) | 0.90(0.16) |
| F-025 + FVIII-C2 | ND | ND | ND | ND | ND | <0.2 |
| C-019 | 4.07 | 61% | −9% | −1% | 49% | 1.62 |
| C-019 + FVIII-C2 | 1.25 | 63% | −8% | −3% | 48% | 1.52 |
| C-028 | 0.94 | 19% | 14% | −1% | 68% | 8.17 |
| C-028 + FVIII-C2 | 0.74 | 16% | 18% | −2% | 69% | 4.18 |
| Primary binding to FVIII siganl (in RU) does not match summed IgG1 + IgG2 + IgG3 + IgG4 signal (in RU) | | | | | | |
| H-001 | 0.22 | 56% | 29% | −4% | 19% | 2.54 |
| H-001 + FVIII-C2 | 0.15 | 56% | 34% | −5% | 15% | 0.96 |
| Autoimmune Subjects | | | | | | |
| Q-011-001 | 0.96 | 79% | 4% | −1% | 18% | 34.25 |
| Q-011-001 + FVIII-C2 | 0.98 | 79% | 4% | −1% | 18% | 33.19 |
| Q-012-001 (n = 4) | 1.02(4%) | 6%(1%) | 2%(4%) | −1%(0%) | 94%(5%) | 6.40(3.66) |
| Q-012-001 + FVIII-C2 | 1.23 | 2% | −4% | −1% | 103% | 2.78 |
| Q-033 (n = 2) | 0.75(6%) | 82%(1%) | 6%(1%) | −1%(0%) | 13%(0%) | 23.97 |
| Q-033 + FVIII-C2 | 0.85 | 89% | 2% | −1% | 10% | 11.39 |
| Q-016 (n = 2) | 0.96(1%) | 23%(1%) | 8%(1%) | −1%(0%) | 70%(3%) | 26.88 |
| Q-016 + FVIII-C2 (n = 2) | 1.02(3%) | 23%(1%) | 5%(2%) | −1%(0%) | 72%(3%) | 11.19(1.54) |

*ND = Not Determined because the low total IgG titer made estimates of ratios and % Ig subtypes unreliable.

Quantitative results for % IgG subtype, ratio of primary to secondary binding signal (%), and total anti-FVIII IgG (µg/ml) for matched samples with and without the addition of saturating (1 µM) recombinant FVIII-C2. Note that the total anti-FVIII IgG concentrations are corrected for pre analytical dilution factors and reflect the concentration in undiluted plasma. Likewise values >0.2 µg/ml (the lower limit of quantification) are reported based on the assay dynamic range corrected for the sample dilution factor.

TABLE 2

Analysis of serial samples

| Subj # | FVIII-C2 competition assay | Time since inhibitor diagnosis | IgG1 + 2 + 3 + 4 (RU)/ polyclonal IgG (RU) | % IgG$_1$ | % IgG$_2$ | % IgG$_3$ | % IgG$_4$ | Total anti-FVIII IgG from SPR (µg/ml) |
|---|---|---|---|---|---|---|---|---|
| Q-011 | | day 1 | 0.96 | 79% | 4% | −1% | 18% | 34.25 |
| | | day 4 | 0.96 | 71% | 9% | −1% | 22% | 27.43 |
| | | 4 wk | 1.20 | 78% | 5% | −1% | 18% | 22.49 |
| | | 6 wk (n = 3) | 1.09(30%) | 69%(4%) | 10%(1%) | −2%(1%) | 23%(2%) | 6.02(3.79) |
| | | 8 wk (n = 3) | 1.17(74%) | 72%(7%) | 10%(2%) | −1%(3%) | 19%(3%) | 1.36(0.95) |
| | | 22 wk (n = 2) | 0.97(5%) | 89%(7%) | 4%(2%) | −2%(2%) | 9%(4%) | 0.94(0.11) |
| | | 32 wk (n = 2) | 1.04(3%) | 83%(1%) | 2%(0%) | −1%(0%) | 15%(1%) | 1.58(0.35) |
| Q-012 | | day 1 (n = 4) | 1.02(4%) | 6%(1%) | 2%(4%) | −1%(0%) | 94%(5%) | 6.40(3.66) |
| | | day 7 | 1.00 | 6% | 5% | −1% | 90% | >23.50 |

TABLE 2-continued

Analysis of serial samples

| Subj # | FVIII-C2 competition assay | Time since inhibitor diagnosis | IgG1 + 2 + 3 + 4 (RU)/ polyclonal IgG (RU) | % IgG$_1$ | % IgG$_2$ | % IgG$_3$ | % IgG$_4$ | Total anti-FVIII IgG from SPR (μg/ml) |
|---|---|---|---|---|---|---|---|---|
| | | day 9 (n = 3) | 0.99(6%) | 6%(0%) | 5%(1%) | 1%(1%) | 90%(0%) | 8.90(4.14) |
| | | day 13 (n = 2) | 0.99(11%) | 7%(0%) | 4%(0%) | 0%(1%) | 89%(1%) | 6.72(1.97) |
| | | 26 wk | ND | ND | ND | ND | ND | <0.2 |
| | | 34 wk | ND | ND | ND | ND | ND | <0.2 |
| | | 42 wk | ND | ND | ND | ND | ND | <0.2 |
| Q-015 | (−) FVIII-C2 | 1 wk | 1.00 | 101% | 0% | −1% | −1% | 31.39 |
| | (+) FVIII-C2 | | 0.70 | 102% | 0% | −1% | −1% | 9.11 |
| | (−) FVIII-C2 | 3 wk | 1.05 | 101% | 1% | −1% | 0% | 23.54 |
| | (+) FVIII-C2 | | 0.74 | 104% | −1% | −3% | −1% | 1.42 |
| | (−) FVIII-C2 | 51 wk | 1.04(1%) | 99%(0%) | 1%(0%) | (1%)(0%) | 1%(0%) | 5.49(0.09) |
| | (+) FVIII-C2 | | ND | ND | ND | ND | ND | <0.2 |
| | (−) FVIII-C2 | 5 yrs | 1.11(2%) | 95%(2%) | 0%(1%) | −1%(0%) | 5%(1%) | 3.11(0.62) |
| | (+) FVIII-C2 | | ND | ND | ND | ND | ND | <0.2 |
| L-006 | | 1 wk | 0.87 | 92% | 4% | 4% | 0% | 11.85 |
| | | 5 wk (n = 2) | 0.98(1%) | 91%(2%) | 2%(4%) | 4%(0%) | 3%(2%) | 13.13(1.46) |
| | | 9 wk | 0.98 | 85% | 6% | 2% | 7% | 11.97 |
| | | 21 wk | ND | ND | ND | ND | ND | <1.09 |
| | | 35 wk | ND | ND | ND | ND | ND | <0.99 |

ND = Not Determined because the low total IgG titer made estimates of ratios and % Ig subtypes unreliable.

Quantitative results for % IgG subtype, ratio of primary to secondary binding signal (%), and total anti-FVIII IgG (μg/ml) for serial samples from subjects Q-011, Q-012, Q-015 and L-006. Results from paired samples with and without the addition of 1 μM soluble FVIII-C2 are reported for subject Q-015, the only subject that demonstrated a change in the proportion of anti-FVIII-C2 antibodies over time.

TABLE 3

Clinical data for subjects

| Subject | Age | HA Severity | Baseline FVIII | Peak Titer (BU/ml) | Inhibitor Treatment History | Hemophilia Genotype (if known) |
|---|---|---|---|---|---|---|
| Predominantly IgG1 Response | | | | | | |
| Q-015 | 24 | mild | 6-14% | 250 | ITI failed | A2201P |
| N-008 | 2 | moderate | 3% | 11 | no ITI | 14-21 del |
| L-006 | 2 | moderate | 1% | 87 | ITI initiated | R2304C |
| Predominantly IgG4 Response | | | | | | |
| F-014 | 19 | severe | <1% | 32 | ITI partly successful | int-22 inv |
| B-002 | 20 | severe | <1% | 667 | ITI failed | 9-11 del |
| A-002 | 14 | severe | <1% | 256 | ITI failed | not inversion |
| Mixed IgG Subtype Response | | | | | | |
| G-004 | 16 | severe | <1% | 1000+ | no ITI | int-22 inv |
| C-010 | 27 | severe | <1% | 80 | ITI partly successful | not inversion |
| D-006 | 10 | severe | <1% | 496 | ITI failed | not inversion |
| L-025 | 35 | severe | <1% | 191 | no ITI | not inversion |
| P-011 | 8 | severe | <1% | 1084.4 | ITI failed | int-22 inv |
| P-001 | 12 | severe | <1% | 308.7 | ITI failed | int-22 inv |
| F-006 | 27 | severe | <0.25% | 44 | no ITI | int-22 inv |
| A-008 | 31 | severe | <1% | 86 | ITI successful | int-22 inv |
| F-025 | 21 | severe | <1% | 43.8 | ITI failed | int-22 inv |
| C-019 | 60 | severe | <1% | 336 | ITI failed | int-22 inv |
| C-028 | 2 | severe | <1% | 96 | ITI failed | not inversion |
| Secondary and primary SPR binding signals (in RU) do not match | | | | | | |
| H-001 | 50 | severe | <1% | 742 | no ITI | int-22 inv |
| Autoimmune subjects | | | | | | |
| Q-011 | 77 | autoimmune | normal | 6 | prednisone | autoimmune |
| Q-012 | 77 | autoimmune | normal | 2 | prednisone | autoimmune |
| Q-033 | 79 | autoimmune | normal | 39 | prednisone | autoimmune |
| Q-016 | 62 | autoimmune | normal | 20 | prednisone | autoimmune | not inversion = not an intron-22 or intron-1 inversion mutation;
14-21del = exons 14-21 deleted;
9-11del = exons 9-11 deleted;
int-22 inv = intron 22 inversion;
ITI = Immune Tolerance Induction;
BU/ml = Bethesda Units/milliliter
Demographic and HA-related clinical information regarding the inhibitor-positive subjects.

TABLE 4

| | Sample ID | Date | Sample Type | Normal or Hemophilia A | Fresh or frozen |
|---|---|---|---|---|---|
| 1 | PSBC-005-041-001 | May 7, 2012 | Plasma | Normal | Frozen |
| 2 | PSBC-005-042-001 | May 7, 2012 | Plasma | Normal | Frozen |
| 3 | PSBC-005-019-001 | Apr. 23, 2012 | Plasma | Severe HA | Frozen |
| 4 | PSBC-005-001-002 | Oct. 17, 2012 | Plasma | Normal | Fresh |
| 5 | PSBC-005-001-002 | Oct. 17, 2012 | Serum | Normal | Fresh |

The invention claimed is:

1. A method for determining quantitative isotype distribution of target antigen-specific antibodies of a target antigen-specific antibody response in a subject, the method comprising:
contacting a biorecognition surface with a sample from the subject comprising a plurality of target antigen-specific antibodies to produce a contacted surface, wherein a target antigen is IgG, IgA, IgM, IgE, or Factor VIII (FVIII);
determining a total titer of the target antigen-specific antibodies immobilized on the contacted surface by detecting interaction of the target antigen-specific antibodies with the biorecognition surface with a biosensor device;
contacting the contacted surface with one or more probe antibodies specific for the target antigen-specific antibodies under saturation conditions; and
determining the quantitative isotype distribution of the target antigen-specific antibodies in the sample by detecting interaction of the one or more probe antibodies with the contacted surface with the biosensor device.

2. The method of claim 1, further comprising determining epitope specificity of the target antigen-specific antibodies.

3. The method of claim 1, wherein the biosensor device is a surface plasmon resonance (SPR) device.

4. The method of claim 1, wherein the sample is a plasma sample.

5. The method of claim 1, wherein the sample is a plasma sample treated with caprylic acid (CA).

6. The method of claim 1, wherein the biorecognition surface comprises a surface coupled with a capture agent specific for the target antigen, and wherein the target antigen is contacted by the capture agent.

7. The method of claim 6, wherein the capture agent is a capture antibody.

8. The method of claim 1, further comprising coupling a capture agent specific for the target antigen to a surface and contacting the capture agent with the target antigen to produce the biorecognition surface.

9. The method of claim 1, further comprising comparing the determined total titer of the target antigen-specific antibodies with the determined quantitative isotype distribution of the target antigen-specific antibodies and thereby evaluating the accuracy of the determined quantitative isotype distribution.

10. The method of claim 1, wherein the target antigen-specific antibodies from the sample are anti-Factor VIII (FVIII) antibodies.

11. The method of claim 1, wherein the target antigen is FVIII.

* * * * *